United States Patent
Brodsky

(10) Patent No.: US 11,499,964 B2
(45) Date of Patent: Nov. 15, 2022

(54) ASSAY TO DIAGNOSE AND TREAT DISORDERS OF THE ALTERNATIVE PATHWAY OF COMPLEMENT ACTIVATION

(71) Applicant: THE JOHNS HOPKINS UNIVERSITY, Baltimore, MD (US)

(72) Inventor: Robert Brodsky, Brooklandville, MD (US)

(73) Assignee: The Johns Hopkins University, Baltimore, MD (US)

( * ) Notice: Subject to any disclaimer, the term of this patent is extended or adjusted under 35 U.S.C. 154(b) by 560 days.

(21) Appl. No.: 15/553,826

(22) PCT Filed: Feb. 29, 2016

(86) PCT No.: PCT/US2016/020066
§ 371 (c)(1),
(2) Date: Aug. 25, 2017

(87) PCT Pub. No.: WO2016/138520
PCT Pub. Date: Sep. 1, 2016

(65) Prior Publication Data
US 2018/0246082 A1    Aug. 30, 2018

Related U.S. Application Data

(60) Provisional application No. 62/198,187, filed on Jul. 29, 2015, provisional application No. 62/121,706, filed on Feb. 27, 2015.

(51) Int. Cl.
| | |
|---|---|
| *A61K 39/395* | (2006.01) |
| *G01N 33/50* | (2006.01) |
| *C07K 16/18* | (2006.01) |
| *A61P 7/00* | (2006.01) |

(52) U.S. Cl.
CPC ............ *G01N 33/5091* (2013.01); *A61P 7/00* (2018.01); *C07K 16/18* (2013.01); *C07K 2317/24* (2013.01); *C07K 2317/76* (2013.01); *G01N 2440/00* (2013.01); *G01N 2800/22* (2013.01)

(58) Field of Classification Search
None
See application file for complete search history.

(56) References Cited

U.S. PATENT DOCUMENTS

| | | |
|---|---|---|
| 2009/0004183 A1 | 1/2009 | Taylor et al. |
| 2012/0258474 A1 | 10/2012 | Tatnell et al. |
| 2015/0239838 A1 | 8/2015 | Phadke et al. |
| 2015/0239868 A1 | 8/2015 | Pais et al. |
| 2015/0239893 A1 | 8/2015 | Wang et al. |
| 2015/0239894 A1 | 8/2015 | Gadhachanda et al. |
| 2015/0239895 A1 | 8/2015 | Gadhachanda et al. |
| 2015/0239919 A1 | 8/2015 | Gadhachanda et al. |
| 2015/0239920 A1 | 8/2015 | Gadhachanda et al. |
| 2015/0239921 A1 | 8/2015 | Wiles et al. |
| 2019/0241617 A1* | 8/2019 | Francois .................. C07K 7/08 |
| 2020/0095578 A1* | 3/2020 | Hinkle ............... A61K 39/3955 |

OTHER PUBLICATIONS

Harboe et al. (2008) J. Cell. Mol. Med. 12: 1074-1084.*
Pu et al., Paroxysmal nocturnal hemoglobinuria from bench to bedside., Clinical and Translational Science (2011), 4 (3), 219-224.
Brodsky, Narrative Review: paroxysmal nocturnal hemoglobinura: the phsyiology of complement-related hemolytic anemia., Annals of Internal Medicine (2008), 148(8), 587-596.
Savage et al., Glycosylphosphatidylinositol-anchored protein deficiency confers resistance to apoptosis in PNH., Experimental Hematology (2009), 37(1), 42-51.
Subias et al., A novel antibody against human factor B that blocks formation of the C3bB proconvertase and inhibits complement activation in disease models., The Journal of Immunology (2014), 193(11), 5567-5575.
Gavriilaki et al., Modified Ham test for atypical hemolytic uremic syndrome., Blood (2015), 125(23), 3637-646.
Taylor et al., Anti-glycophorin single-chain Fv fusion to low-affinity mutant erythropoietin improves red blood cell-lineage specificity., Protein Engineering, design & selection (2010), 23(4), 251-60.
Cataland et al., The use of ADAMTS13 activity, platelet count, and serum creatinine to differentiate acquired thrombotic thrombocytopenic purpura from other thrombotic microangiopathies., Br J Haematol (2012), 157(4) 501-3.
Coppo et al., Predictive Features of Severe Acquired ADAMTS13 Deficiency in Idiopathic Thrombotic Microangiopathies: The French TMA Reference Center Experience., PLoS one (2010), 5(4), e10208.
Goktas et al., Evaluating ESWL-induced renal injury based on urinary TNF-α, IL-1α, and IL-6 levels., Urol Res. (2012), 40(5), 569-73.

(Continued)

*Primary Examiner* — Michael D Pak
(74) *Attorney, Agent, or Firm* — Johns Hopkins Technology Ventures

(57) ABSTRACT

The present invention relates generally to the field of disorders of complement activation. More specifically, the present invention provides methods and compositions useful for diagnosing and treating atypical hemolytic uremic syndrome, antiphospholipid antibody syndrome and other disorders of the alternative pathway of complement activation. In one embodiment, a method comprises the steps of (a) incubating or contacting serum obtained from a patient suspected of having atypical hemolytic uremic syndrome (aHUS) with a glycosylphosphatidylinositol-anchored protein (GPI-AP) deficient cell line; and (b) performing a cell viability assay on the cells from step (a). In a specific embodiment, the method further comprises the step of diagnosing the patient as having aHUS based on a statistically significant increased difference of non-viable cells from the patient serum as compared to a control.

11 Claims, 20 Drawing Sheets

(56) References Cited

OTHER PUBLICATIONS

Noris et al., Dynamics of complement activation in aHUS and how to monitor eculizumab therapy., Blood (2014), 124 (11), 1715-26.
Rodriguez et al., Genetics of atypical hemolytic uremic syndrome (aHUS)., Seminars in thrombosis and hemostasis (2014)., 40(4), 422-30.
Legendre et al., Terminal complement inhibitor eculizumab in atypical hemolytic-uremic syndrome., N Engl J Med. (2013)., 368(23), 2169-81.
Wada et al., Natural history of thrombotic thrombocytopenic purpura and hemolytic uremic syndrome., Seminars in thrombosis and hemostasis (2014), 40(8), 866-73.
Scully et al., How I treat thrombotic thrombocytopenic purpura and atypical haemolytic uraemic syndrome., Br. J. Haematol. (2014), 164(6), 759-66.
Crawley et al., Thrombotic thrombocytopenic purpura: basic pathophysiology and therapeutic strategies Hematology/the education program of the American Society of Hematology American Society of Hematology Education Program (2013)., 292-9.
Brodsky, Robert A., Narrative review:: paroxysmal nocturnal hemoglobinuria: the physiology of complement-related hemolytic anemia', Annals of Internal Medicine, 2008, vol. 148, No. 8, pp. 587-595.
Gavriilaki, Eleni et al., 'Modified Ham test for atypical hemolytic uremic syndrome', Blood, Jun. 4, 2015, vol. 125, No. 23, pp. 3637-3646.
Pu, Jeffrey J. et al., 'Paroxysmal nocturnal hemoglobinuria from bench to bedside', Clinical and Translational Science, 2011, vol. 4, Issue 3, pp. 219-224.
Savage, William J. et al., 'Glycosylphosphatidylinositol-anchored protein deficiency confers resistance to apoptosis n PNH', Experimental Hematology, 2009, vol. 37, No. 1, pp. 42-51.
Subias, Marta et al., 'A novel antibody against human factor B that blocks formation of the C3bB proconvertase and inhibits complement activation in disease models', The Journal of Immunology, 2014, vol. 193, No. 11, pp. 5567-5575.

\* cited by examiner

| PATIENT CLINICAL CHARACTERISTICS ||||||||||||
|---|---|---|---|---|---|---|---|---|---|---|---|
| NO | AGE, GENDER | DIAGNOSIS (TRIGGER) | PHASE (WEEKS) | ADAMTS 13 ACTIVITY (%) | ADAMTS 13 INHIBITOR (%) | PLT COUNT (x10³/μl) | LDH (mg/dl) | Cr (mg/dl) | GENETIC MUTATION | PREVIOUS TREATMENTS | CURRENT TREATMENT | RESPONSE TO TREATMENT | %NON-VIABLE CELLS |
| 1 | 47, F | aHUS (KIDNEY STONE) | ACUTE | 75 | NA | 9 | 2505 | 2.3 | CFHR3-CFHR1 HOMOZYGOUS DELETION; CFH HETEROZYGOUS c.2850G>T, p.Gln950His | - | - | - | NA |
| 1 | 47, F | aHUS (KIDNEY STONE) | REMISSION (20 w) | NA | NA | 314 | 228 | 1.9 | CFHR3-CFHR1 HOMOZYGOUS DELETION; CFH HETEROZYGOUS c.2850G>T, p.Gln950His | PEx (x5) | | NO | 63 |
| 1 | 47, F | aHUS (KIDNEY STONE) | REMISSION (20 w) | NA | NA | 314 | 228 | 1.9 | CFHR3-CFHR1 HOMOZYGOUS DELETION; CFH HETEROZYGOUS c.2850G>T, p.Gln950His | ECULIZUMAB (x8) | - | YES | 63 |
| 2 | 52, F | aHUS (PANCREATITIS) | ACUTE | 47 | NA | 13 | 1276 | 3.0 | CFHR3-CFHR1 HETEROZYGOUS DELETION; ADAMTS13 HETEROZYGOUS c.2195C>T, p.Ala732Val | - | METHYLPREDNISOLONE, PEx | NO | NA |
| 2 | 52, F | aHUS (PANCREATITIS) | REMISSION (14 w) | NA | NA | 187 | 190 | 1.0 | CFHR3-CFHR1 HETEROZYGOUS DELETION; ADAMTS13 HETEROZYGOUS c.2195C>T, p.Ala732Val | METHYLPREDNISOLONE, PEx (x3) | ECULIZUMAB (x14) | YES | 24 |
| 3 | 64, M | aHUS (UNKNOWN) | ACUTE | 59 | NA | 66 | 1288 | 2.5 | NONE | - | - | - | NA |
| 3 | 64, M | aHUS (UNKNOWN) | REMISSION (1 w) | NA | NA | 237 | 216 | 1.3 | NONE | PEx (x14) RITUXIMAB | ECULIZUMAB (x7) | YES | 28 |
| 4 | 38, F | aHUS (UNKNOWN) | ACUTE | >100 | NA | 78 | 858 | 6.8 | CFH NM_000186: HETEROZYGOUS c.472G>A,p.Val158Ile; HETEROZYGOUS c.3079G>C,p.Ala1027Pro; CFHR3-CFHR1 HETEROZYGOUS DELETION; ADAMTS13 NM_139025: HETEROZYGOUS c.2420+3G>A; HETEROZYGOUS c.3677C>T,p.Thr1226Ile | - | - | - | 46 |
| 4 | 38, F | aHUS (UNKNOWN) | RESPONDING | >100 | <5 | 110 | 248 | 4.3 | CFH NM_000186: HETEROZYGOUS c.472G>A,p.Val158Ile; HETEROZYGOUS c.3079G>C,p.Ala1027Pro; CFHR3-CFHR1 HETEROZYGOUS DELETION; ADAMTS13 NM_139025: HETEROZYGOUS c.2420+3G>A; HETEROZYGOUS c.3677C>T,p.Thr1226Ile | HEMODIALYSIS PEx(x5), PREDNISOLONE | ECULIZUMAB (x2) | YES | 39 |

FROM FIG. 1A

| # | Age,Sex | Disease | Phase | | | | | | Genetics | Treatment 1 | Treatment 2 | | |
|---|---|---|---|---|---|---|---|---|---|---|---|---|---|
| 5 | 59, M | aHUS | ACUTE | 22 | NA | 39 | 676 | 2.3 | NONE | PEx (x4) | - | NO | 42 |
| | | (HODGKIN'S DISEASE) | RESPONDING | 22 | NA | 114 | 197 | 1.4 | | PEx (x4) | ECULIZUMAB (x2) BRENTUXIMAB | YES | 41 |
| | | | REMISSION (1 w) | NA | NA | 307 | 180 | 1.6 | | PEx (x4) | ECULIZUMAB (x7) | YES | 34 |
| 6 | 65, F | aHUS (QUININE) | ACUTE | 71 | NA | 24 | 209 | 7.8 | CFHR3-CFHR1 HETEROZYGOUS DELETION; CD46 NM_0022389 HETEROZYGOUS c.424G>C, p.Glu142Gln | - | HEMODIALYSIS, PEx | NO | NA |
| | | | REMISSION (36 w) | NA | NA | 445 | 168 | 1.1 | | PEx (x3) HEMODIALYSIS, ECULIZUMAB (x5) | NONE | NO / YES | 32 |
| 7 | 35, F | aHUS (LIVER TRANSPLANT) | ACUTE | NA | NA | NA | NA | NA | NONE | - | - | - | NA |
| | | | REMISSION | NA | NA | 108 | 75 | 1.1 | | - | ECULIZUMAB (x77) | YES | 42 |
| 8 | 23, F | aHUS | ACUTE | 102 | NA | 62 | 2820 | 6.3 | NONE | - | - | - | NA |
| | | | REMISSION (60 w) | NA | NA | 205 | 178 | 3.5 | | ECULIZUMAB (x37) | HEMODIALYSIS | YES | 49 |
| 9 | 24, F | TTP | ACUTE | 6 | 82 | 111 | 556 | 1.0 | CFHR3-CFHR1 HOMOZYGOUS DELETION; | - | PREDNISONE, PEx(x10), RITUXIMAB (x3) | - | NA |
| | | | RESPONDING | 100 | 23 | 303 | 744 | 1.1 | | PREDNISONE, PEx (x10), RITUXIMAB (x3) | AZATHIOPRINE 100mg/d PREDNISONE | YES | 2 |
| 10 | 42, M | TTP | ACUTE | <5 | 59 | 8 | 1408 | 1.4 | NONE | - | PREDNISONE | - | 8 |
| | | | REMISSION (3 w) | <5 | 31 | 156 | 195 | 1.0 | | PREDNISONE, PEx(x10), RITUXIMAB | - | YES | 17 |
| 11 | 23, M | TTP | ACUTE | 9 | NA | 26 | 732 | 1.0 | CFHR3-CFHR1 HETEROZYGOUS DELETION; ADAMTS13 | - | NONE | - | NA |
| | | | REMISSION (1 w) | 9 | 33 | 209 | 113 | 1.1 | | - | PEx (X11) | YES | 1 |
| | | | REMISSION | 8 | NA | 228 | 126 | 1.1 | | PEx (X11) | PREDNISONE | YES | 2 |

FROM FIG. 1B

| | | | | | | | | | | | | |
|---|---|---|---|---|---|---|---|---|---|---|---|---|
| | | | (8w) | | | | | HETEROZYGOUS c.2384G>T, p.Ala795Val; HETEROZYGOUS c.1368G>T, p.Gln456His | | | | |
| 12 | 50, F | TTP | ACUTE | <5 | 90 | 7 | NA | 0.8 | NONE | PEx, RITUXIMAB(x4), PREDNISONE, AZATHIOPRINE | PEx | - | NA |
| | | | REMISSION (24w) | NA | NA | 173 | 186 | 0.8 | | PEx, RITUXIMAB(x4), PREDNISONE, AZATHIOPRINE | - | YES | 12 |
| 13 | 64, F | TTP | ACUTE | <5 | 18 | 7 | 1109 | 1.1 | NONE | PREDNISONE, PEx (7) | NO | NA |
| | | | REMISSION | NA | NA | 324 | NA | 1.0 | | PREDNISONE, PEx(x12), RITUXIMAB (x4) | NONE | YES | 8 |
| 14 | 42, F | TTP | ACUTE | <5 | 57 | 61 | 331 | 0.8 | NONE | - | PREDNISONE | - | NA |
| | | | REMISSION | 40 | 20 | 365 | NA | 1.0 | | PREDNISONE, (x4), RITUXIMAB | - | YES | 7 |
| 15 | 35, F | TTP | ACUTE | <5 | 96 | 5 | 2200 | NA | NA | - | - | - | 3 |
| 16 | 45, F | TTP | ACUTE | <5 | 75 | 12 | 1100 | NA | NA | - | - | - | 1 |
| 17 | 85, F | Stec-HUS | ACUTE | 59 | 27 | 6 | 1662 | 3.0 | NONE | - | NONE | NA | NA |
| | | | REMISSION | NA | 33 | 124 | 465 | 1.6 | | PEx, PREDNISONE | ECULIZUMAB (x3) | YES | 24 |
| 18 | 31, M | aPIGN | ACUTE | 84 | NA | 234 | 138 | 2.2 | CFHR3-CFHR1 HETEROZYGOUS DELETION; CFH NM_000186; HETEROZYGOUS c.2850G>t,p.Gln950His ADAMTS13 NM_139205: HETEROZYGOUS c.2758A>G,p.Met920Val | - | PREDNISONE | NO | 19 |
| 19 | 36, F | DIC | ACUTE | NA | NA | 120 | 333 | 1.9 | NA | | NONE | NO | 6 |

F: FEMALE; M: MALE; CFHR: COMPLEMENT FACTOR H RELATED PROTEINS; CFH: COMPLEMENT FACTOR H; ADAMTS13: A DISINTEGRIN AND METALLOPROTEASE WITH THROMBOSPONDIN TYPE 1 MOTIF, 13; aHUS: ATYPICAL HEMOLYTIC UREMIC SYNDROME; TTP: THROMBOTIC THROMBOCYTOPENIC PURPURA, aPIGN: ATYPICAL POST-INFECTIOUS GLOMERULONEPHRITIS; Stec-HUS: SHIGA-TOXIN ASSOCIATED HEMOLYTIC UREMIC SYNDROME; DIC: DISSEMINATED INTRAVASCULAR COAGULATION, NA: NOT AVAILABLE; PEx PLASMA EXCHANGE

FIG. 1C

| TENNESSEE CRITERIA | MISSISSIPPI CRITERIA |
|---|---|
| MICROANGIOPATHIC HEMOLYTIC ANEMIA, LDH > 600 | HEMOLYSIS (INCREASED LDH AND ANEMIA) |
| PLATELET COUNT < 100,000 CELLS/MICROL | PLATELET COUNT < 150,000 CELLS/MICROL |
| TOTAL BILIRUBIN > 1.2 mg/dL or LDH > 600 IU/L<br>AST > 70 IU/L | LDH > 600 IU/L, AST > 40 IU/L AND/OR ALT > 40 IU/L |

FIG. 12

| ID | DIAGNOSIS | GESTATIONAL AGE (WEEKS) | RACE | AGE (YEARS) | BMI (kg/m²) | SBP* (mmHg) | DBP* (mmHg) | AST (IU/L) | ALT (IU/L) | PROTEINURIA | PLT (x10³/μl) | LDH (mg/dl) | CREATININE (mg/dl) | NEONATAL WEIGHT | % WEIGHT | SGA NEONATE | % KILLING |
|---|---|---|---|---|---|---|---|---|---|---|---|---|---|---|---|---|---|
| 1 | CLASSIC HELLP (GROUP 1) | 34.2 | CAUCASIAN | 23 | 24.3 | 162 | 96 | 84 | 68 | YES | 132 | 325 | 0.7 | 1790 | 5 | YES | 50 |
| 2 | | 30.6 | CAUCASIAN | 32 | 24 | 155 | 90 | 109 | 79 | NA | 73 | 260 | 0.7 | 1490 | 15 | NO | 0 |
| 3pp | | PPD 1 | AFRICAN AMERICA | 25 | 31.1 | 200 | 100 | 1485 | 952 | YES | 52 | 1623 | 0.6 | 1190 | 1 | YES | 33 |
| 4pp | | PPD 4 | AFRICAN AMERICA | 27 | 32.1 | 174 | 98 | 95 | 80 | YES | 214 | 303 | 1 | 1880 | 25 | NO | 21 |
| 5 | ATYPICAL HELLP (GROUP 2) | 30.2 | AFRICAN AMERICA | 27 | 41.86 | 215 | 105 | 43 | 52 | YES | 180 | 276 | 1.6 | 1040 | 1 | YES | 48 |
| 6 | | 28.2 | AFRICAN AMERICA | 25 | 44.1 | 200 | 100 | 106 | 57 | YES | 272 | 449 | 1.1 | 1125 | 50 | NO | 41 |
| 7 | | 30.5 | ASIAN | 28 | 22.5 | 193 | 77 | 17 | 18 | YES | 135 | 231 | 0.9 | 1420 | 1 | YES | 0 |
| 8 | | 36.1 | AFRICAN AMERICA | 35 | 25.8 | 184 | 100 | 10 | 7 | YES | 117 | 316 | 0.7 | 2410 | 25 | NO | 33 |
| 9 | | 24.6 | AFRICAN AMERICA | 25 | 32.5 | 172 | 106 | 89 | 147 | YES | 204 | 440 | 1 | 380 | 1 | YES | 6 |
| 10 | PREECLAMPSIA WITH SEVERE FEATURES (GROUP 3) | 36.5 | CAUCASIAN | 34 | 40.9 | 175 | 93 | 37 | 22 | YES | 163 | 202 | 0.5 | 2310 | 8 | YES | 0 |
| 11 | | 33.2 | AFRICAN AMERICA | 19 | 22.1 | 170 | 110 | 22 | 13 | YES | 238 | 240 | 0.8 | 1730 | 3 | YES | 20 |
| 12 | | 31.6 | AFRICAN AMERICA | 30 | 22.4 | 188 | 109 | 17 | 13 | YES | 160 | 271 | 1 | 1760 | 40 | NO | 25 |
| 13 | | 40.2 | CAUCASIAN | 29 | 48.4 | 204 | 96 | 17 | 14 | NO | 272 | NA | 0.6 | 4390 | 99 | NO | 19 |
| 14 | | 32.1 | CAUCASIAN | 20 | 51.7 | 180 | 103 | 20 | 13 | YES | 241 | 223 | 0.8 | 1810 | 9 | YES | 0 |
| 3ap | | 31.1 | AFRICAN AMERICA | 25 | 31.1 | 200 | 100 | 31 | 28 | YES | 291 | 222 | 0.6 | 1190 | 1 | YES | 25 |
| 4ap | | 32.4 | AFRICAN AMERICA | 27 | 32.1 | 174 | 98 | 21 | 18 | YES | 168 | 274 | 0.9 | 1880 | 40 | NO | 2 |

BMI: BODY MASS INDEX; SBP: SYSTOLIC BLOOD PRESSURE; DBP: DIASTOLIC BLOOD PRESSURE; AST: ASPARTATE AMINOTRANSFERASE (AST); ALT: ALANINE AMINOTRANSFERASE (ALT); PLT: PLATELET COUNT; LACTATE DEHYDROGENASE (LDH); SGA: SMALL GESTATIONAL AGE; NA: NOT AVAILABLE; ANTEPARTUM (AP); POSTPARTUM (PP); POSTPARTUM DAY (PPD); * DEFINES HIGHEST ANTEPARTUM VALUE; DEFINES LOWER ANTEPARTUM VALUE; ALL LAB VALUES CORRELATE WITH THE DAY OF BLOOD DRAW FOR CELL KILLING

FIG. 13

ASSAY TO DIAGNOSE AND TREAT DISORDERS OF THE ALTERNATIVE PATHWAY OF COMPLEMENT ACTIVATION

CROSS-REFERENCE TO RELATED APPLICATIONS

This application is a 35 U.S.C. § 371 U.S. national entry of International Application PCT/US2016/020066, having an international filing date of Feb. 29, 2016, which claims the benefit of U.S. Provisional Application No. 62/121,706, filed Feb. 27, 2015, and U.S. Provisional Application No. 62/198,187, filed Jul. 29, 2015, the content of each of the aforementioned applications is herein incorporated by reference in their entirety.

FIELD OF THE INVENTION

The present invention relates generally to the field of disorders of complement activation. More specifically, the present invention provides methods and compositions useful for diagnosing and treating atypical hemolytic uremic syndrome, antiphospholipid antibody syndrome and other disorders of the alternative pathway of complement activation.

BACKGROUND OF THE INVENTION

Thrombotic microangiopathies (TMAs) present with thrombocytopenia, non-immune hemolytic anemia, peripheral blood schistocytes, and often other end-organ damage to the kidneys and central nervous system. TMAs are frequently life-threatening and have considerable clinical overlap so prompt recognition of the underlying pathophysiology is critical. After exclusion of TMAs due to underlying diseases such as disseminated intravascular coagulation (DIC), drugs, or malignancy or scleroderma-associated renal crisis, the differential diagnosis is often between thrombotic thrombocytopenic purpura (TTP) and hemolytic uremic syndrome (HUS).

TTP results from impaired post-secretion processing of ultra large von Willebrand factor multimers due to severe deficiency of a disintegrin and metalloprotease with thrombospondin type 1 motif, 13 (ADAMTS13). Severe ADAMTS13 deficiency (usually defined as <10%) may be inherited (Upshaw-Schulman syndrome) or acquired, resulting from IgG autoantibodies directed against ADAMTS13. Without treatment TTP may lead to neurologic impairment, renal failure and death. Acquired TTP is much more common than Upshaw-Schulman syndrome and is best treated with plasma exchange.

HUS is classified as typical versus atypical, and most cases are associated with acute kidney injury. Typical HUS is caused by Shiga toxin producing organisms (most commonly *Escherichia coli* and *Shigella dysenteriae*). The mainstay of therapy is supportive care. Atypical HUS (aHUS) is most commonly caused by defects in the regulation of the alternative pathway of complement (APC). These defects are usually inherited but may also be acquired. Affected patients may have lifelong systemic complications leading to damage of multiple organ systems (renal, gastrointestinal, central nervous system, cardiac) and death. Although plasma exchange may be effective in some cases, underlying complement-mediated damage to the kidneys and central nervous system often persists. Within one year after diagnosis, more than 50% of patients treated with plasma exchange or plasma infusion experience permanent renal damage, progress to end-stage renal disease, or die. Terminal complement inhibition with the monoclonal antibody, eculizumab, is highly effective for treating aHUS and is now considered the treatment of choice for this disease.

In patients presenting with TMAs it is important to obtain ADAMTS13 levels and screen for Shiga toxin before instituting definitive therapy. Plasma exchange is often initiated before the results of these assays return due to the aggressiveness of TMAs. If ADAMTS13 activity is less than 10% a diagnosis of TTP is established, especially if an inhibitor of ADAMTS13 is also detected, then daily plasma exchange is continued. If ADAMTS13 activity is greater than 10% and Shiga toxin assay is negative, a diagnosis of aHUS must be considered.

Unfortunately, there is no definitive test to make a diagnosis of aHUS and given the high cost of eculizumab definitive therapy is often delayed or not administered. Genetic testing for mutations that lead to increased activation of APC is expensive, takes several weeks to obtain results and is only informative in roughly 50-60% of cases. Frequently, genetic variants of unknown significance are identified, providing clinicians with data of uncertain utility. More recently biomarkers of APC such as C5a or soluble C5b9 have been compared in aHUS and TTP but these are not reliable in distinguishing the two diseases.

SUMMARY OF THE INVENTION

The present invention is based, at least in part, on the development of an assay to distinguish atypical hemolytic uremic syndrome (aHUS) from other microangiopathic hemolytic anemias (MAHA). aHUS is a rare MAHA that often leads to renal failure, stroke and premature death. In most cases the disease is caused by genetic mutation in one of more than 6 genes that leads to increased activation of the alternative pathway of complement. Currently there is no good diagnostic assay for aHUS; thus, the disease is often confused with other MAHAs such as thrombotic thrombocytopenic purpura (TTP), malignant hypertension, pre-eclampsia, disseminated intravascular coagulation, and catastrophic anticardiolipin syndrome. Making a prompt diagnosis is critical because aHUS is effectively treated by eculizumab, a drug that costs more than $20,000 dollars a dose. Thus, physicians and hospitals are understandably reluctant to release the drug without a more certain diagnosis. We have developed a simple, rapid, and inexpensive assay to reliably distinguish aHUS from other MAHAs within 1-2 days of clinical presentation.

Accordingly, in one embodiment, a method comprises the steps of (a) incubating serum obtained from a patient suspected of having atypical hemolytic uremic syndrome (aHUS) with a plurality of glycosylphosphatidylinositol-anchored protein (GPI-AP) deficient cells; and (b) performing a cell viability assay on the cells from step (a). In a specific embodiment, the method further comprises the step of diagnosing or identifying the patient as having or likely to have aHUS based on a statistically significant increased difference of non-viable cells from the patient serum as compared to a control. In another embodiment, the method further comprises generating a report of the cell viability assay of step (b). In an alternative embodiment, the performing step of step (b) comprises generating a report of the cell viability assay.

In certain embodiments, the plurality of GPI-AP deficient cells is a Phosphatidylinositol glycan class A (PIGA) null cell line. In a specific embodiment, the plurality of GPI-AP deficient cells line is a cell line including, but not limited to, endothelial cells such as the TF-1 cell line. In another embodiment, the plurality of GPI-AP deficient cells is a PIGA null induced pluripotent stem cell line. In other embodiments, the plurality of GPI-AP deficient cells are obtained by biochemical treatment of cells to remove GPI-AP, for example, phosphatidylinositol-specific phospholipase C (PIPLC)-treated endothelial cells. In certain embodiments, the cell line is genetically or biochemically modified to remove complement regulatory proteins on the cell surface. For example, cell lines that are missing CD59 and/or CD55 that naturally protect cells from complement-mediated destruction could be used. Primary cells could also be used.

In particular embodiments, the cell viability assay comprises a cell viability indicator that is colorimetric or fluorescent. In a specific embodiment, the cell viability assay is the WST-1 cell viability assay.

In another embodiment of the present invention, a method for diagnosing aHUS in a patient comprises the steps of (a) incubating serum obtained from a patient suspected of having aHUS with a plurality of GPI-AP deficient cells; (b) performing a cell viability assay on the cells from step (a); and (c) diagnosing or identifying the patient as having aHUS based on a statistically significant increased difference of non-viable cells from the patient serum as compared to a control. In a specific embodiment, a method for treating aHUS in a patient comprises the steps of administering an effective amount of a terminal complement inhibitor to a patient diagnosed with aHUS according to a method described herein. In particular embodiments, the terminal complement inhibitor comprises eculizumab. In a more specific embodiment, a method for treating aHUS in a patient comprises the step of administering an effective amount of eculizumab to a patient diagnosed with aHUS based on the performance of a cell viability assay on a plurality of GPI-AP deficient cells that have been incubated with serum obtained from the patient, wherein the diagnosis is based on a statistically significant increased difference of non-viable cells from the patient serum as compared to a control.

In particular embodiments, a method for treating aHUS in a patient comprises the steps of (a) incubating serum obtained from a patient suspected of having aHUS with a plurality of GPI-AP deficient cells; (b) performing a cell viability assay on the cells from step (a); (c) diagnosing the patient as having aHUS based on a statistically significant increased difference of non-viable cells from the patient serum as compared to a control; and (d) administering an effective amount of eculizumab to the patient.

In another aspect, the presently disclosed assay can also be used to diagnose and treat other disorders of the alternative pathway of complement activation, particularly, over-activation of the alternative pathway of complement. The methods and kits of the present invention can be used to identify patients who should be treated with a complement inhibitor, to monitor treatment progress for a patient taking a complement inhibitor or otherwise stratifying a patient for treatment. For example, the present invention can also be used to diagnose and treat typical HUS, antiphospholipid antibody syndrome (APS), catastrophic antiphospholipid antibody syndrome (CAPS), post-infectious glomerulonephritis, macular degeneration, and HELLP syndrome (hemolysis, elevated liver enzymes and low platelets). Although several embodiments are described herein for aHUS, it is understood that such embodiments are applicable to other disorders or conditions associated with alternative pathway of complement activation including the above-recited conditions. In addition, it is understood that treatment of a patient determined to have a disorder or condition associated with over-activation of the alternative pathway of complement can be treated not only with eculizumab, but with any terminal complement inhibitor including, but not limited to protetase inhibitors, soluble complement regulators, therapeutic antibodies, complement component inhibitors, and receptor antagonists. Specific examples of complement inhibitors include, but are not limited to, C1-Inh (Cetor/Sanquin, BerinertP/CSL Behring, Lev Pharma), Rhucin/rhCl1NH (Pharming Group N.V.), sCR1/TP10 (Avant Immunotherpeutics), CAM-2/MLN-2222 (Millenium Pharmaceuticals), eculuizumab/soliris (Alexion Pharmaceuticals), Pexelizumab (Alexion Pharmaceuticals), Ofatumumab (Genmab A/S), APL-2 (Apellis Pharmaceuticals), sDAF, sMCP, sMCP-DAF, sCD59, DAF-cd59, C5a mutants, Antii-05, Anti-C3, Anti-C3a, Anti-05a, NMeFKPdChaWdR, F-(OpdChaWR), Compastatin/POT-4 (Potentia Pharmaceuticals), OMS721 (Omeros Corporation), AMY-101 (Amyndas Pharmaceuticals SA), PMX-53 (Peptech Ltd.), rhMBL (Enzon Pharmaceuticals), BCX-1470, FUT-175, K-76 and Thioester inhibitors. Complement inhibitors can also include factor D inhibitors such as ACH-4471 (Achillion Pharmaceuticals, Inc. (New Haven, Conn.)). Other Achillion complement inhibitors are described in U.S. Patent Application Publications No. 20150239921, No. 20150239920, No. 20150239919, No. 20150239895, No. 20150239894, No. 20150239893, No. 20150239868, and No. 20150239838. The methods and kits described herein can be used to treat, stratify or otherwise identify patients for administration with complement inhibitors including the foregoing list.

In certain embodiments, the present invention provides methods for diagnosing and treating antiphospholipid antibody syndrome (APS). In one embodiment, a method comprises the steps of (a) incubating serum obtained from a patient suspected of having APS with a plurality of GPI-AP deficient cells; and (b) performing a cell viability assay on the cells from step (a). In a specific embodiment, the method further comprises the step of diagnosing the patient as having APS based on a statistically significant increased difference of non-viable cells from the patient serum as compared to a control.

In certain embodiments, the plurality of GPI-AP deficient cells a cell line including, but not limited to, an endothelial cell line such as the TF-1 cell line. In particular embodiments, the plurality of GPI-AP deficient cells is a PIGA null cell line. It is understood, however, that other mutant cells/cell lines can be used so long as the mutation (e.g., in another area of PIGA or another gene) results in GPI-AP deficiency. In a specific embodiment, the GPI-AP deficient cell line is the TF-1 cell line. In other embodiments, the GPI-AP deficient cell line is a biochemically GPI-AP deficient cell line, for example, phosphatidylinositol-specific phospholipase C (PIPLC)-treated endothelial cells. In certain embodiments, the cell line is genetically or biochemically modified to remove complement regulatory proteins on the cell surface. For example, cell lines that are missing CD59 and/or CD55 that naturally protect cells from complement-mediated destruction could be used. Primary cells could also be used.

In particular embodiments, the cell viability assay comprises a cell viability indicator that is colorimetric or fluorescent. In a specific embodiment, the cell viability assay is the WST-1 cell viability assay.

In another embodiment of the present invention, a method for diagnosing APS in a patient comprises the steps of (a) incubating serum obtained from a patient suspected of having APS with a plurality of GPI-AP deficient cells; (b) performing a cell viability assay on the cells from step (a); and (c) diagnosing the patient as having APS based on a statistically significant increased difference of non-viable cells from the patient serum as compared to a control. In a specific embodiment, a method for treating APS (or symptoms thereof including blood dotting) in a patient comprises the steps of administering an effective amount of one or more of anticoagulants, statins and rituximab, to a patient diagnosed with APS according to a method described herein. Anticoagulants can include warfarin, heparin, aspirin, dabigatran, rivaroxaban, and apixaban. In particular embodiments, APS can be treated with the terminal complement inhibitor eculizumab. In a more specific embodiment, a method for treating APS in a patient comprises the step of administering an effective amount of an anticoagulant, statin, rituximab, and/or eculizumab to a patient diagnosed with APS based on the performance of a cell viability assay on a plurality of GPI-AP deficient cells that have been incubated with serum obtained from the patient, wherein the diagnosis is based on a statistically significant increased difference of non-viable cells from the patient serum as compared to a control.

In particular embodiments, a method for treating APS in a patient comprises the steps of (a) incubating serum obtained from a patient suspected of having APS with a plurality of GPI-AP deficient cells; (b) performing a cell viability assay on the cells from step (a); (c) diagnosing the patient as having APS based on a statistically significant increased difference of non-viable cells from the patient serum as compared to a control; and (d) administering an effective amount of an anticoagulant, statin, rituximab, and/or eculizumab to the patient.

In yet another embodiment, a method comprises the steps of (a) incubating serum obtained from a patient suspected of having a disorder or condition associated with over-activation of the alternative pathway of complement with a plurality of GPI-AP deficient cells; and (b) performing a cell viability assay on the cells from step (a). In a further embodiment, the method further comprises the step of diagnosing or identifying the patient a disorder or condition associated with over-activation of the alternative pathway of complement on a statistically significant increased difference of non-viable cells from the patient serum as compared to a control. In particular embodiments, the disorder or condition associated with over-activation of the alternative pathway of complement comprises aHUS, typical HUS, APS, CAPS, post-infectious glomerulonephritis, macular degeneration, and HELLP syndrome. The method can further comprise recommending, prescribing, treating or administering a terminal complement inhibitor.

In another aspect, the present invention provides kit for conducting the assays described herein. In particular embodiments, the kit comprises a plurality of GPI-AP deficient cells. In another embodiment, the kit can also comprise growth media for the cell line. The kit can further comprise a substrate or support for containing the cells. In other embodiments, the kit comprises a positive and negative control. The kit can also comprise the necessary buffers for preparing, washing, etc. of the samples and/or cells. In a specific embodiment, the kit also comprises the components for conducting the cell viability assay including the cell proliferation reagent (e.g., WST-1), cell viability indicator reagent and the like. The kit can also comprise instructions for carrying out the methods described herein.

In a general aspect, the present invention provides an assay comprising the steps of (a) incubating a plurality of GPI-AP deficient cells with serum activated for the alternative complement pathway; and (b) performing a cell viability assay on the cells of step (a). In certain embodiments, the GPI-AP deficient cell line incubated with serum is also incubated with a candidate complement inhibitor. In certain embodiments, the serum is obtained from a patient having a disorder or condition associated with over-activation of the alternative pathway of complement. In other embodiments, the serum comprises cobra venom factor activated serum. Thus, the assay of the present invention can be used to screen or test candidate complement inhibitors.

BRIEF DESCRIPTION OF THE FIGURES

FIG. 1 is a table containing patient characteristics at initial diagnosis and post-treatment.

FIG. 2A shows flow cytometric analysis of CD59 expression on ADP-activated endothelial cells treated with PIPLC versus not treated endothelial cells. After trypsinization endothelial cells were recovered in cell culture medium at 37° C. for 30 minutes, treated with PIPLC and then, stained with anti-CD59 antibody. Reduced CD59 expression on PIPLC treated cells is shown. FIGS. 2B-2E show confocal microscopy of ADP-activated endothelial cells treated with PIPLC and stained with C5b-9 (depicted in red) and DAPI (blue) as nuclei cell counterstaining. Magnification 40×. C5b-9 deposition is shown after incubation with atypical hemolytic uremic syndrome (aHUS) serum (B) compared to heat-inactivated aHUS serum (C), thrombotic thrombocytopenic purpura (TTP) serum (D) and normal serum (E).

FIG. 5A is a comparison of non-viable cells between TF-1 wild type and TF-1 PIGA null cells (data are presented as mean with SEM) after incubation with normal and aHUS serum. FIG. 5B shows the percentage of non-viable PIGA null TF1 cells among different disease entities (data are presented as mean with SEM). Serum from aHUS patients induces significantly increased percentages of non-viable cells compared to healthy controls (p<0.001) and TTP (p<0.001). CVF: cobra venom factor activated serum; aHUS: atypical hemolytic uremic syndrome (grey triangles symbolizes values of aHUS patients treated with eculizumab; whereas black triangles aHUS in acute phase or remission); TTP: thrombotic thrombocytopenic purpura; aPIGN: atypical post-infectious glomerulonephritis; Stec-HUS: Shiga-toxin associated hemolytic uremic syndrome; DIC: Disseminated intravascular coagulation.

FIG. 6A shows a similar percentage of non-viable TF1 cells (p=0.459) among aHUS patients in different disease status (acute phase, eculizumab treatment, remission). FIG. 6B shows the effects of different dilutions of eculizumab treated serum on cell viability (1:1, 1:2, 1:4, 1:8, 1:16). All aHUS patients showed no increase in killing at 1:1 and 1:16 dilutions; two of the three aHUS patients had no increase in killing at 1:2; and all three aHUS patients showed increased killing at 1:4 and 1:8 dilutions. Serum from a PNH patient treated with eculizumab presented no increase in killing at any dilution (shown in grey). aHUS: atypical hemolytic uremic syndrome; PNH: paroxysmal nocturnal hemoglobinuria; Ecu-aHUS: aHUS patient treated with eculizumab.

FIG. 9A. Loss of CD59 expression on PIGA null iPS cells versus wild type iPS cells. FIG. 9B. Incubation with serum activated for the alternative complement pathway (cobra venom factor activates serum or serum from atypical hemolytic syndrome) in the modified Ham test. PIGA null and MCAHS2 neurons are highly susceptible to complement activation compared to wild type iPS cells. Cobra venom (factor induces complement activation); aHUS (atypical hemolytic syndrome with increased complement activation).

FIG. 11A. Increased percentage of non-viable cells in the modified Ham test was observed in the acute phase of Shiga-toxin associated HUS (stec-HUS1a). The same patient was tested twice after resolution of the syndrome (4 and 7 days after the first sample, symbolized as stec-HUS1b and c), showing normalization of cell killing. Similarly, a second patient (stec-HUS2) tested after resolution of the syndrome showed low percentage of cell killing. The dotted line symbolizes the cut-off value (21.5% non-viable cells) above which percentage of non-viable cells suggests increased complement activation observed in atypical HUS. Results from two independent experiments are shown. FIG. 11B. Eculizumab containing serum (ECU) was collected within 60 minutes of eculizumab infusion from a PNH patient. ECU was mixed with serum from the acute shiga-toxin associated HUS in different percentages (50-50%, 25-75% and 12.5-87.5% of HELLP and ECU sera respectively). Total amount of serum in the assay remained unchanged (20%). Eculizumab containing serum resulted in a normalization of the modified Ham test results in all ratios. Results from two independent experiments are shown. FIG. 11C. Recombinant shiga-toxin 2 from $E.$ $coli$ was added in normal serum (NS) to replicate the effects of shiga-toxin associated HUS. Addition of shiga-toxin (stx) resulted in increased percentage of non-viable cells compared to normal serum alone and with heat-inactivated shiga-toxin (hi-stx), as well as heat-inactivated normal serum (HNS) with maximum amount of shiga-toxin. Results from two independent experiments are shown.

FIG. 12. Tennessee and Mississippi Criteria for HELLP Syndrome. Lactate dehydrogenase (LDH), aspartate aminotransferase (AST), alanine aminotransferase (ALT).

FIG. 13. Laboratory and clinical characteristics of participants with preeclampsia with severe features at the time of sample collection.

FIG. 15A. Participants with classic HELLP showed significantly increased percentage of cell killing compared to participants with preeclampsia with severe features but no HELLP and compared to normal controls (38.7±9.8% versus 13.0±11.7% and 4.1±7.3%, p=0.048 and p=0.020 respectively). FIG. 15B. The receiver operating characteristic (ROC) curve for HELLP diagnosis by the modified Ham test showed a significant area under the curve (0.781, p-value=0.019). A percentage of nonviable cells higher than 20.5% was determined as a cut-off value for the diagnosis of HELLP with 66.7% sensitivity and 88.9% specificity. The blue line defined the area under the curve for the modified Ham test, whereas the green diagonal line is the reference line of no discrimination that would be produced by a completely random guess.

DETAILED DESCRIPTION OF THE INVENTION

Figure 2A:
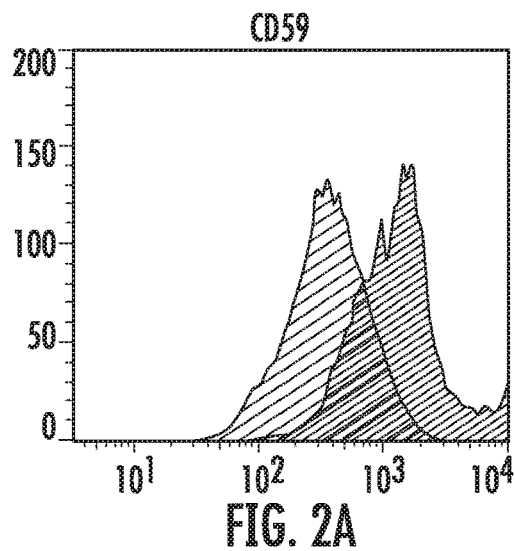
FIGS. 2A-2E depict C5b9 deposition on phosphatidylinositol-specific phospholipase C (PIPLC) treated human endothelial cells.
Figure 2B:
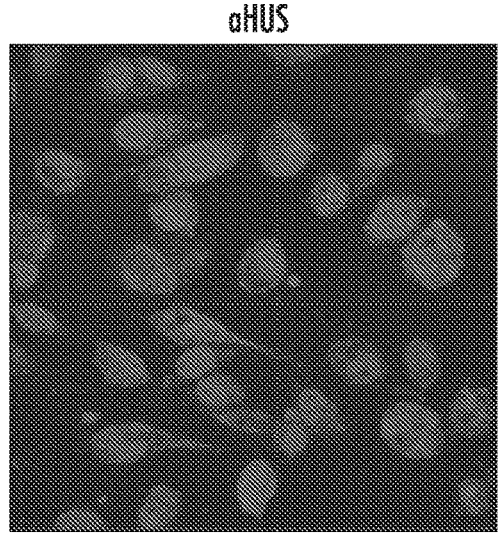
Figure 2C:
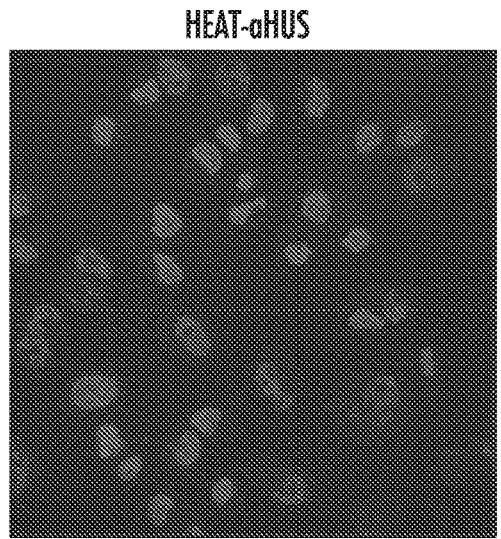
Figure 2D:
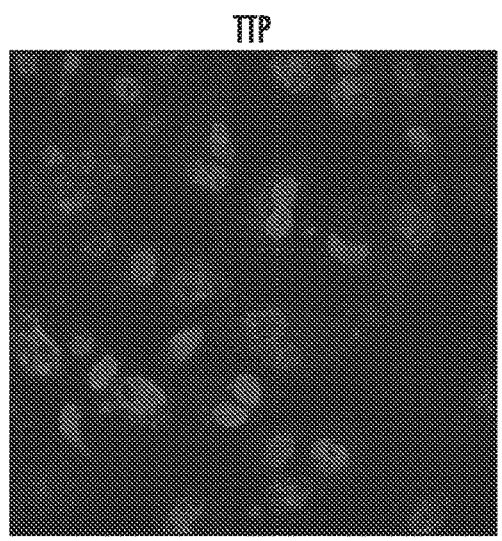
Figure 2E:
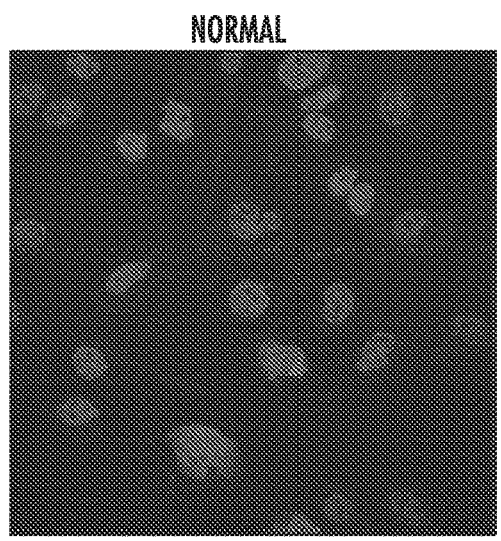
Figure 3A:
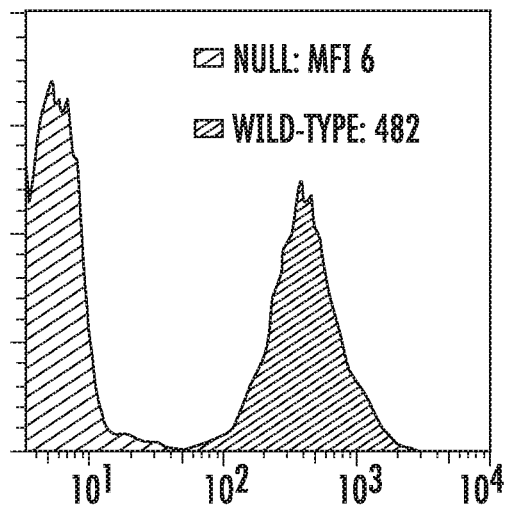
FIGS. 3A-3D depict C5b9 deposition by flow cytometry on PIGA null TF-1 cells A. Loss of CD59 expression on PIGA null TF-1 cells versus wild type TF-1 cells B. C5b-9 deposition after incubation with acute TTP serum (black) versus heat-inactivated control (light grey). C. C5b-9 deposition after incubation with serum from a patient with aHUS in remission (black) compared to heat-inactivated control (light grey). D. C5b-9 depositions after incubation with serum from a second patient with acute aHUS (black) compared to heat-inactivated control (light grey).
Figure 3B:
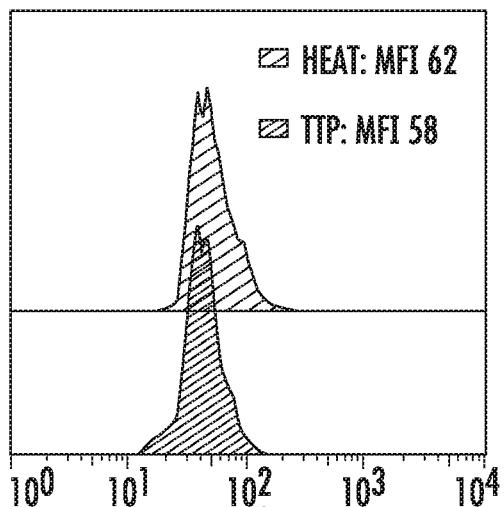
Figure 3C:
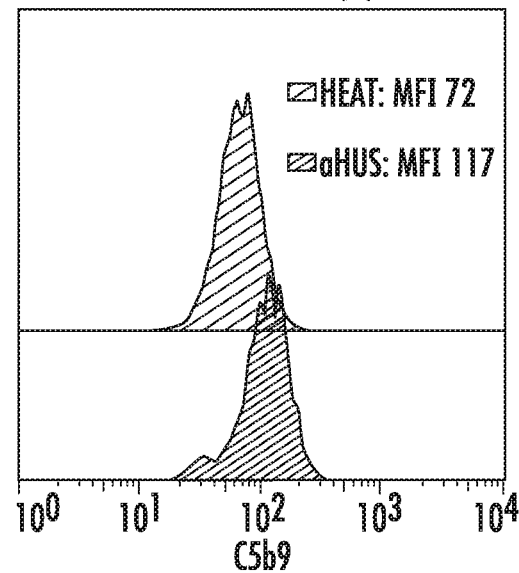
Figure 3D:
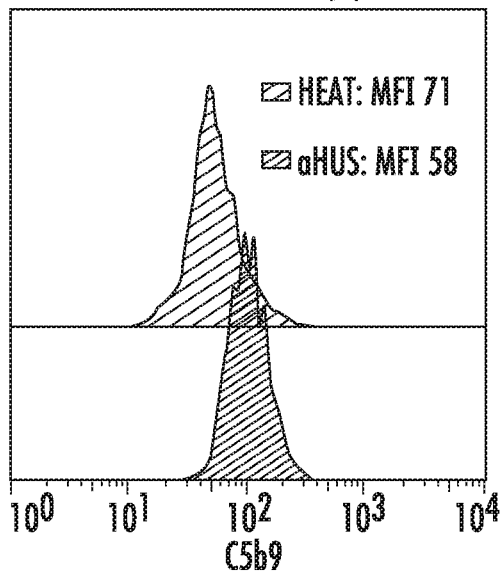

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "gene" is a reference to one or more genes, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

Currently, the diagnosis of aHUS is one of exclusion. When a patient presents with a MAHA it is recommended to initiate plasma exchange and to send an ADAMTS13 activity level to exclude TTP and a shiga toxin assay to exclude typical HUS. These assays often take 2-5 days to return. If the ADAMTS13 level is <10 the diagnosis of TTP is fairly certain and it is recommended to continue with plasma exchange. If the ADAMTS13 level is over 30% it is fairly certain that TTP is not the diagnosis. Levels between 10 and 30 are equivocal. Moreover, aHUS patients often show improvement in their LDH levels and platelet counts while on plasma exchange but end-organ damage (CNS, renal etc.) usually does not improve making it hard to know whether the patient is truly responding or not. Delay in receiving drugs that block terminal complement can lengthen hospital stay and result in severe end organ damage (stroke, renal failure etc.) or even death. Our novel complement assay that only requires patient serum allows one to distinguish between aHUS and TTP (the major differential diagnosis for MAHAs) within a day allowing physicians to choose the most appropriate therapy much earlier. Genetic testing for mutations in complement related genes can make a diagnosis of aHUS, but only ~50% of aHUS patients have mutations. Furthermore, genetic testing is expensive and takes more than a month to get the results. Importantly, this assay is likely to be helpful in assessing other diseases where there is over-activation of the alternative pathway of complement. Examples include antiphospholipid antibody syndrome, post-infectious glomerulonephritis, macular degeneration, etc.

Microangiopathic hemolytic anemias (MAHAs) often present with similar clinical manifestation; however, the pathophysiology and treatment of MAHAs is highly specific. Two commonly confused MAHAs are aHUS and TTP. TTP is usually caused by antibodies to ADAMTS13 leading to accumulation of large molecular weight multimers that cause endothelial damage, severe thrombocytopenia, neurologic manifestations, and a severe hemolytic anemia. TTP is effectively treated in most cases with plasma exchange. aHUS is usually caused by mutations in genes that either inhibit regulation of the alternative pathway of complement or by mutations that directly activate the alternative pathway of complement. Often a "trigger" such as infection, autoimmunity, cancer, pregnancy or surgery precedes the diagnosis of aHUS. Thus, patients have a genetic predisposition (increased activation of the alternative pathway of complement) and a triggering event that increases systemic complement levels. aHUS patients present similarly to TTP patients. They often present with a MAHA, severe thrombocytopenia, renal insufficiency and mental status changes. Genetic testing is expensive (~$10,000 dollars), takes weeks to months to get the results, and only identifies a causative mutation in about 50% of cases. Plasma exchange is effective for a small percentage of patients with aHUS. The most effective therapy is inhibition of terminal complement with the FDA approved drug eculizumab; however, there is reluctance to start this highly expensive drug therapy (~$20,000 dollars a dose) without a clear diagnosis. This often leads to delay in treatment, prolonged hospital stays and often renal failure or death. Thus, one of the biggest needs in the management of MAHAs is a method for measuring the activity of the alternative pathway of complement in the serum and to distinguish aHUS from other MAHAs such as TTP.

As described herein, we report on the methods for an inexpensive, rapid, diagnostic assay to measure the complement activation and to distinguish aHUS from TTP and other MAHAs. We previously established a PIGA mutant cell line derived from TF1 cells. PIGA is a gene required for the first step in the biosynthesis of glycosylphosphatidylinositol (GPI), a lipid moiety that anchors dozens of proteins to the cell surface. Two of the GPI-anchored proteins that are defective in the TF1 cell line are CD55 and CD59. The proteins both regulate complement. CD55 blocks C3 convertases and CD59 interferes with/blocks terminal complement activation. Our new technology uses this cell line as a reporter cell line for activation of complement in patient serum. Briefly, we collect 5 cc of serum from patients, dilute it 1:4 with growth medium and measure viability of the PIGA mutant TF1 cells after 30 minutes using a WST1 assay. To confirm that the cell kill is associated with complement we stain the cells with a monoclonal antibody to C5b9 (terminal complement attack) and assay the staining by flow cytometry.

In a non-limiting embodiment, the assay may be conducted as follows:

Blood is collected in serum separation tubes and is immediately centrifuged at 4° C. Serum is separated and stored at −80° C. Heat inactivation is performed the same day of the experiment, incubating the serum at 56° C. for 30 minutes.

The cell viability assay is performed on a glycosylphosphatidylinositol-anchored proteins (GPI-AP) deficient TF-1 cell line that has been previously established in our laboratory. See Savage et al., 37(1) EXP. HEMATOL. 42-51 (2009). Cells are maintained in RPMI 1640 medium supplemented with 2 ng/mL GM-CSF, 2 mM 1-glutamine, penicillin/streptomycin, and 10% fetal calf serum under BL2 lab containment.

Cells are plated in a U-shaped 96-well plate at a density of approximately 4.000 cells/well and cultured until confluent. Then, cells are washed with PBS and incubated with serum at a concentration of 1:4 for 30 minutes at 37° C. Serum is diluted in GVB (gelatin veronal buffer, Sigma). Cells are washed again with PBS and incubated with the cell proliferation reagent (4-[3-(4-lodophenyl)-2-(4-nitrophenyl)-2H-5-tetrazolio]-1.3-benzene disulfonate/WST-1, Roche) for 3 hours at 37° C. Wst-1 is diluted in the cell culture medium at a concentration of 1:10 and 100 μl of Wst-1 solution is added per well. Absorbance is measured in a microplate (ELISA) reader at 450 nm with a reference wavelength at 650 nm, according to the manufacturer's instructions and previous publication. See Taylor et al., 23(4) PEDS 251-60 (2010). The colorimetric assay is based on cleavage of the tetrazolium salt, WST-1, by mitochondrial dehydrogenases in viable cells.

Absorbance values of each sample are normalized after subtraction of the absorbance value of a blank cell. Percentage of viable cells is expressed as a ratio of the absorbance of each sample multiplied by 100, to the absorbance of the same sample's heat-inactivated control. Percentage of dead cells is calculated after subtracting percentage of viable cells from 100.

The cell viability indicator can be any substance, composition or compound capable of providing a particular change which selectively identifies the presence of viable cells in the biological sample. In particular embodiments, the cell viability indicator is a tetrazole. Tetrazoles serve as a substrate for an enzymatic reaction, which provides a colorimetric measure of the activity of cellular metabolic enzymes that reduce the tetrazoles to formazan. Such tetrazoles include, but are not limited to, 3-(4,5-Dimethylthiazol-2-yl)-2,5-diphenyltetrazolium bromide (MTT), 2,3-bis-(2-methoxy-4-nitro-5-sulfophenyl)-2H-tetrazolium-5-carboxanilide (XTT), 3-(4,5-dimethylthiazol-2-yl)-5-(3-carboxymethoxyphenyl)-2-(4-sulfo-phenyl)-2H-tetrazolium (MTS) or Water soluble Tetrazolium salts (WTSs), for example WST-1 (2-(4-Iodophenyl)-3-(4-nitrophenyl)-5-(2,4-disulfophenyl)-2H-tetraz-olium) and WST-8 (2-(2-methoxy-4-nitrophenyl)-3-(4-nitrophenyl)-5-(2,4-disulfophenyl)-2H-t-etrazolium).

Other suitable cell viability indicator reagents may also be used. In certain embodiments of the invention, biological samples are exposed to fluorescent dyes to provide information regarding the biological function of the cells within the sample. Such fluorescent dyes include "live cell" dyes (e.g., calcein AM) which selectively accumulate within viable cells and which are modified within the environment of viable cells to produce fluorescent chemical species. Such "live cell" dyes selectively render viable cells fluorescent whilst leaving non-viable cells unstained. Variants of these "live cell" dyes have chemical groups such that they become covalently attached to cellular proteins during fixation so that the dye is retained within the cell for prolonged periods of time. Other fluorescent dyes include "dead cell" dyes (e.g., propidium iodide or ethidium bromide homodimer) which can enter and stain non-viable cells but which are excluded from viable cells.

In further embodiments, assays that are based on the incorporation of labeled nucleotide or nucleotide analogs into the DNA of cells can be used. In such assays, cells are exposed to a labeled nucleotide, e.g., $^{14}$C-thymidine, 3H-thymidine, or 5-bromo-2-deoxyuridine (BrdU). Proliferation is quantified by measuring the amount of labeled nucleotide taken up by the cells. Radiolabeled nucleotides can be measured by radiodetection methods; antibodies can be used to detect incorporation of BrdU.

Still other assays measure cellular viability/proliferation as a function of ATP production. For example, the luciferase enzyme catalyzes a bioluminescent reaction using the substrate luciferin. The amount of bioluminescence produced by a sample of cells measures the amount of ATP present in the sample, which is an indicator of the number of cells.

The present invention also provides kits for performing the assays described herein. In particular embodiments, the kit comprises a GPI-AP deficient cell line. In another embodiment, the kit can also comprise growth media for the cell line. The kit can further comprise a substrate or support for containing the cells. In other embodiments, the kit comprises a positive and negative control. The kit can also comprise the necessary buffers for preparing, washing, etc. of the samples and/or cells. In a specific embodiment, the kit also comprises the components for conducting the cell viability assay including the cell proliferation reagent (e.g., WST-1), cell viability indicator reagent and the like.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1: Assay for Atypical Hemolytic Uremic Syndrome

Materials and Methods

Study's Population.

Patients assessed in the Johns Hopkins University Department of Medicine-Division of Hematology from August 2014 until February 2015 with the differential diagnosis of TMA were enrolled. Patients were clinically categorized as aHUS if their first manifestation of the syndrome met the following criteria: (1) platelet count <100×10$^9$/L, (2) serum creatinine >2.25 mg/dL, and (3) ADAMTS13 activity >10%. These criteria have been proposed in previous studies to clinically differentiate patients with aHUS (Cataland et al., 157(4) Br. J. Haematol. 501-03 (2012); and Coppo et al., 5(4) PLoS One e10208 (2010)). Final diagnosis, course and patient treatment were recorded. All patients gave written informed consent and were enrolled in our TMA Registry. This study was approved by the Institutional Review Board and was conducted in accordance with the Declaration of Helsinki.

Healthy subjects were recruited from the community as controls. Following initial experiments, normal human AB serum (H4522, Sigma-Aldrich, St. Louis, Mo.) was used in control samples.

Blood was collected in serum separation tubes and was immediately centrifuged at 4° C. Serum was separated and stored at −80° C. Heat inactivation was performed the same day of the experiment, incubating the serum at 56° C. for 30 minutes.

Cell Lines.

Endothelial cells (EA.hy926, ATCC® CRL2922™ Manassas, Va.) were cultured in DMEM supplemented with 1 ng/ml of endothelial growth factor (EGF), 2 mM 1-glutamine, penicillin/streptomycin, and 20% fetal calf serum. TF-1 cells (ATCC® CRL2003™, Manassas, Va.) were maintained in RPMI 1640 medium supplemented with 2 ng/mL of granulocyte-macrophage colony-stimulating factor (GM-CSF), 2 mM 1-glutamine, penicillin/streptomycin, and 10% fetal calf serum.

The GPI-anchored protein (GPI-AP) deficient TF-1 cell line has been previously established in our laboratory See Savage et al., 37(1) EXP. HEMATOL. 42-51 (2009). In particular, the TF-1 CD34+ cell line was treated with proaerolysin that lyses cells expressing GPI-AP. Thus, the proaerolysin resistant clone expanded was GPI-AP deficient having a 7 nucleotide deletion at position 291-297 (TTGTCAC) in exon 2 of PIGA resulting in a frameshift mutation.

C5b-9 Imaging by Confocal Microscopy.

50,000 EA.hy926 cells were plated in gelatin-coated sterile glass coverslips and cultured until 80% confluent. ADP activation was performed with 10 µM ADP (0160, Amresco, Solon, Ohio) for 10 minutes at room temperature. GPI anchor cleavage of endothelial cells was performed using phosphatidylinositol-specific phospholipase C (PIPLC, P6466, Life technologies, Carlsbad, Calif.). For these experiments, cells were treated with PIPLC (0.4 unit/ml) for 30 minutes at 37° C. and then incubated with serum for 30 minutes at 37° C. Between steps, cells were washed with Hank's Balanced Salt Solution (24020117, Life technologies, Carlsbad, Calif.). Next, cells were fixed with 4% paraformaldehyde and stained with rabbit anti-complement C5b-9 (204903, Millipore, Bedford, Mass.) followed by Alexa Fluor 594 donkey anti-rabbit IgG secondary antibody (A21207, Life technologies, Carlsbad, Calif.). Counterstaining with DAPI was also performed. C5b9 deposition was subsequently observed in a confocal inverted laser microscope (LSM 510 Meta, Zeiss).

Flow Cytometry Analysis of C5b9 Deposition.

Flow cytometric analysis was performed on EA.hy926 cells treated with PIPLC and GPI-deficient TF1 cell line to assess C5b9 accumulation. Since EA.hy926 cells are adherent, an extra step of trypsinization to single-cell suspension was required as compared to TF-1 suspension cells. Endothelial cells were treated with trypsin (10×, Life technologies, Carlsbad, Calif.) for 3 minutes at 37° C. Of note, surface-attached C5b9 complexes are sensitive to trypsin. Thus, after trypsinization, endothelial cells were recovered in cell culture medium at 37° C. for 30 minutes for 30 minutes at 37° C.

Intracellular staining was performed using the Fix & Perm Cell Fixation and Cell Permeabilization Kit (GAS 001/2, Life technologies, Carlsbad, Calif.). Initial experiments established an optimal incubation period at 10 minutes and serum dilution at 1:4. Cells were labeled with rabbit anti-complement C5b-9 (204903, Millipore, Bedford, Mass.) and a secondary Alexa Fluor 488 donkey anti-rabbit IgG antibody (Jackson ImmunoResearch Laboratories, West Grove, Pa.). C5b9 deposition was analyzed in a BD FACSCalibur with a total number of 10000 events per sample.

Cell Viability Assay.

Cells were plated in 96-well flat bottom plates for endothelial cells or U-shaped 96-well plates for TF1 cells at a density of 4.000 cells/well and cultured until confluent. Endothelial cells were treated with PIPLC, as described above. Then, cells were washed with PBS and incubated with serum in triplicates at a concentration of 1:4 for 30 minutes at 37° C. Serum was diluted in GVB (Gelatin veronal buffer, Sigma-Aldrich, St. Louis, Mo.). Cells were washed again with PBS and incubated with the cell proliferation reagent 4-[3-(4-Iodophenyl)-2-(4-nitrophenyl)-2H-5-tetrazolio]-1.3-benzene disulfonate/WST-1 (Roche, Switzerland) for 2 hours at 37° C. Wst-1 was diluted in the cell culture medium at a concentration of 1:10 and 100 µl of Wst-1 solution was added per well. Absorbance was measured in an iMark Microplate Absorbance Reader (Bio-rad, Hercules, Calif.) at 450 nm with a reference wavelength at 595 nm, according to the manufacturer's instructions and previous publications (Sarica et al., 40(5) UROL RES. (2012)). The colorimetric assay is based on cleavage of the tetrazolium salt, WST-1, by mitochondrial dehydrogenases in viable cells.

Heat-inactivated serum was used as a negative control. Cobra venom factor (CVF, Complement Technology, Tyler, Tex.) which induces activation of the alternative complement pathway was used as a positive control according to manufacturer's instruction.

Reproducibility was investigated by consecutive double testing of five samples.

Data Analysis.

Absorbance values of each sample were normalized after subtraction of the absorbance value of a blank cell. Percentage of viable cells was expressed as a ratio of the absorbance of each sample multiplied by 100, to the absorbance of the same sample's heat-inactivated control. Thus, percentage of non-viable cells was calculated using the following formula: 100−(sample absorbance*100/heat-inactivated sample's absorbance).

Analysis was performed using the Statistical Package for Social Sciences (SPSS) 20.0 for Windows (SPSS, Chicago, Ill.). The independent samples Student t test was used to compare differences between the mean values of two groups. A p value ≤0.05 was considered statistically significant. Analysis of specificity, sensitivity and cutoff value was performed by creating a receiver operating characteristic (ROC curve). Reproducibility was measured using Lin's concordance correlation coefficient.

Results

Patient Population.

Patient characteristics at initial diagnosis and post-treatment are shown in FIG. 1. We studied eleven samples from eight different patients with aHUS (two in acute phase before treatment, six after initiation of eculizumab and three in remission off therapy); ten samples from eight different TTP patients (three in acute phase before treatment, two under treatment with plasma exchange and ongoing TMA, and five in remission no longer on plasma exchange. We also studied serum from a patient with shiga-toxin associated HUS before treatment, a patient with atypical post-infectious glomerulonephritis (PIGN) on prednisone, and a patient with disseminated intravascular coagulation (DIC).

C5b-9 Depositions by Confocal Microscopy and Flow Cytometry.

We initially measured C5b9 deposition after exposure to patient serum on endothelial cells before and after PIPLC treatment. As shown by Noris et al (123(11) BLOOD 1715-26 (2014)), aHUS serum showed increased C5b9 deposition compared to normal serum in non-PIPLC treated cells. In an effort to improve sensitivity and specificity of this effect we treated EA.hy926 with PIPLC before exposing the cells to patient serum. PIPLC-treated EA.hy926 incubated with aHUS serum exhibited increased C5b9 deposition as compared to normal serum, heat-inactivated aHUS serum or TTP serum. Representative images are shown in FIG. 2.

As quantification of C5b9 deposition by immunocytochemistry requires confocal microscopy and further analysis in specialized software, we aimed to easily quantify C5b9 deposition by flow cytometry. It should be noted that initial analysis of surface C5b9 staining showed low levels of deposition and intracellular staining was preferred. Endothelial cells with normal GPI-AP expression displayed a slightly increased mean fluorescent intensity (MFI) of C5b9 staining after incubation with aHUS as compared to heat-inactivated aHUS serum. As expected, PIPLC treated endothelial cells had decreased GPI-AP expression. C5b9 deposition on PIPLC treated endothelial cells showed increased intensity after incubation with aHUS serum compared to the heat-inactivated control.

The above experiments suggested that partial biochemical removal of GPI-AP increased sensitivity to aHUS serum; thus, for future studies we used a PIGA null TF-1 cell line to measure C5b-9 deposition and cell viability following incubation with TMA patient serum. PIGA mutant TF-1 cells have no surface expression of the complement regulatory proteins CD55 and CD59. As shown in FIG. 3, these cells showed increased C5b-9 staining after incubation with aHUS serum as compared to heat-inactivated aHUS serum. Interestingly, similarly increased C5b-9 was observed in aHUS patients at presentation and in remission. In contrast, PIGA null TF-1 cells incubated with TTP serum demonstrated no increase in C5b-9 staining compared to the heat-inactivated control and the normal serum. Results from representative samples are summarized in FIG. 3.

Cell Viability.

Figure 4:
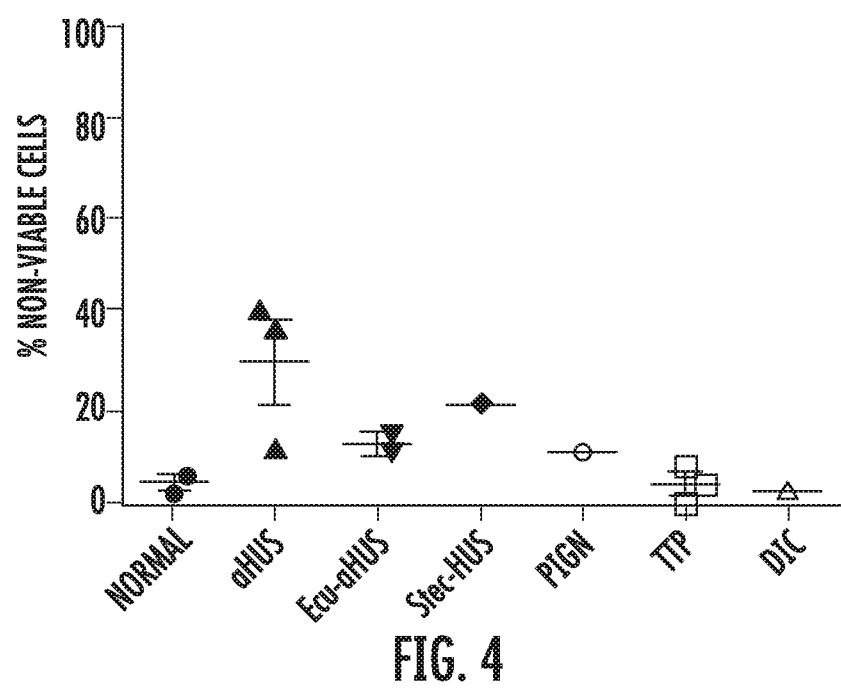
FIG. 4 shows Wst-1 viability assay on PIPLC-treated endothelial cells: Percentage of non-viable PIPLC treated endothelial cells among different disease entities (data are presented as mean with SEM). aHUS: atypical hemolytic uremic syndrome; Ecu-aHUS: atypical hemolytic uremic syndrome treated with eculizumab; TTP: thrombotic thrombocytopenic purpura; aPIGN: atypical post-infectious glomerulonephritis; Stec-HUS: Shiga-toxin associated hemolytic uremic syndrome; EcuPNH: paroxysmal nocturnal hemoglobinuria on eculizumab; DIC: Disseminated intravascular coagulation.

Complement induces cell kill through deposition of the membrane attack complex. In order to establish a simple, rapid, and less subjective assay, we exposed PIPLC-treated endothelial cells and PIGA null TF-1 cells to serum from our TMA patients and measured viability in a WST-1 assay. Cell viability assay was originally performed on endothelial cells treated with PIPLC. Results in the first 11 patients (FIG. 4) demonstrate consistently higher percentages of non-viable cells in patients with aHUS compared to other TMAs or controls.

Figure 5A:
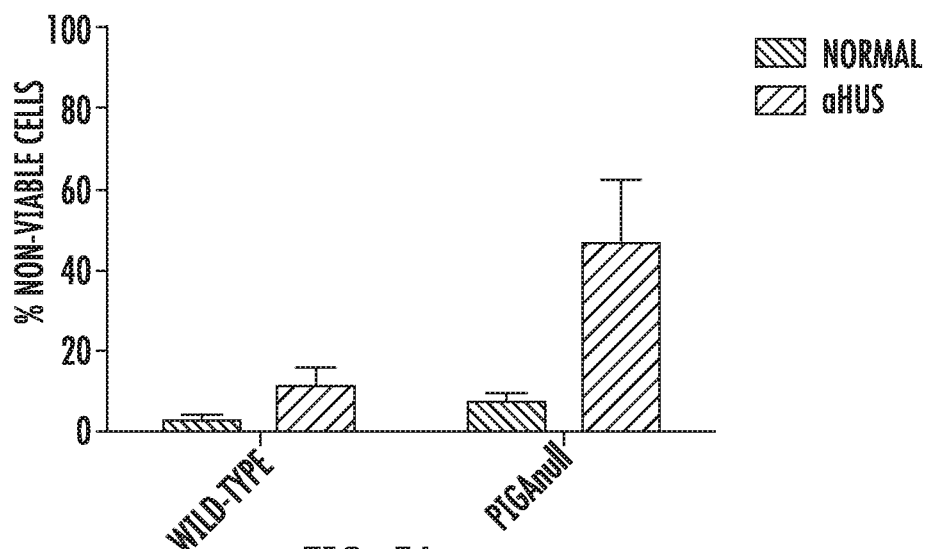
FIGS. 5A-5B depict the genetic disruption of PIGA augments cell killing in aHUS serum
Figure 5B:
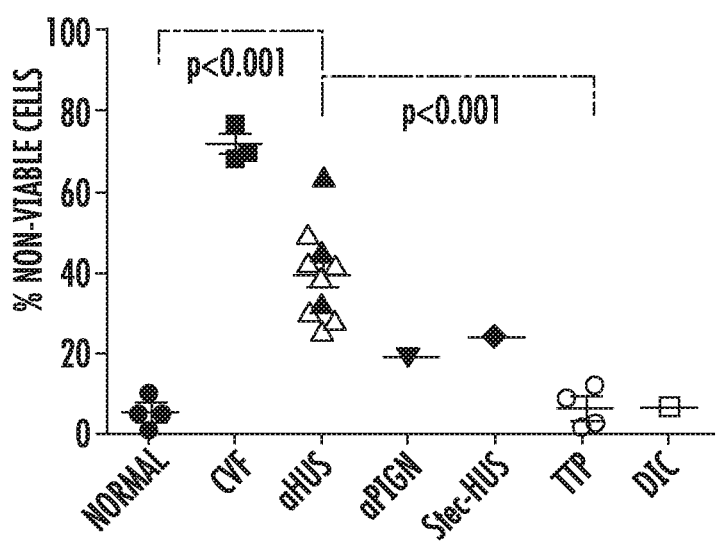

Similar to our studies with C5b-9 deposition, we found the WST-1 killing assay to be more robust on the PIGA null TF-1 cell line. As shown in FIG. 5A, genetic disruption of PIGA gene augmented cell killing in aHUS serum in the PIGA null TF-1 cell line compared to the wild-type TF-1 cells. We next evaluated the sensitivity of the PIGA null TF1 line to complement-mediated killing by serum from a variety of different patients with TMAs. aHUS serum was significantly more toxic to the PIGA null cell line than serum from TTP ($p<0.001$) and healthy controls ($p<0.001$). Heat inactivation abrogated the cell killing and C5b-9 accumulation on the cells demonstrating that the killing was associated with complement activation. As shown in FIG. 5, patients with other TMAs, including TTP and Shiga-toxin associated HUS, had low percentages of non-viable cells in the cell viability assay, similar to levels in healthy controls. Patients with other causes of thrombocytopenia often included in the differential diagnosis of TMAs, such as DIC, also showed low levels of non-viable cells. Intermediate levels of cell viability were found in a patient with atypical PIGN, a disease recently shown to be associated with activation of APC.

Figure 6A:
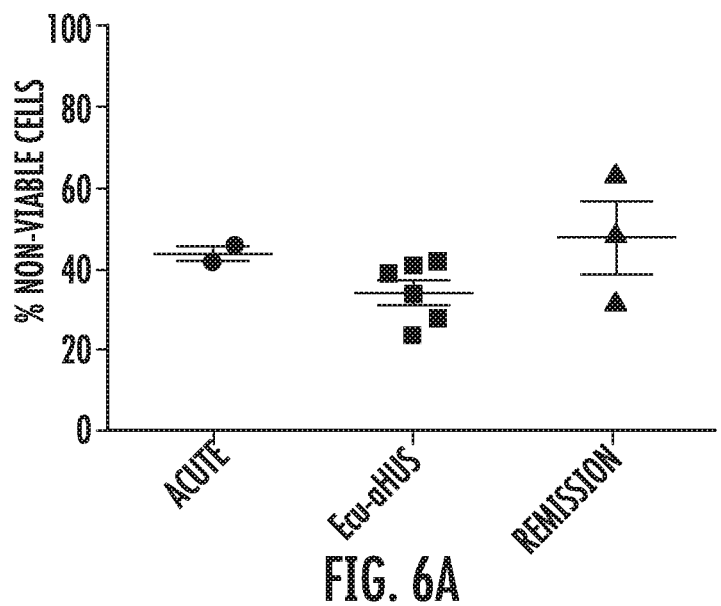
FIGS. 6A-6B depict a Wst-1 cell viability assay in patients with aHUS.
Figure 6B:
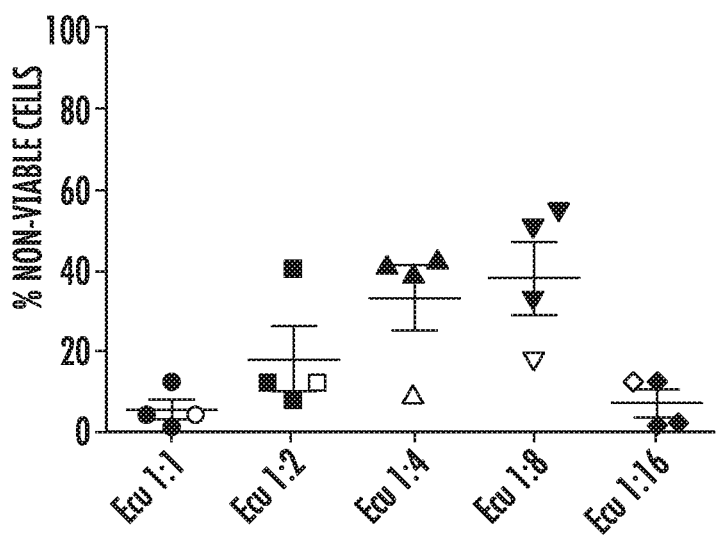
Figure 7:
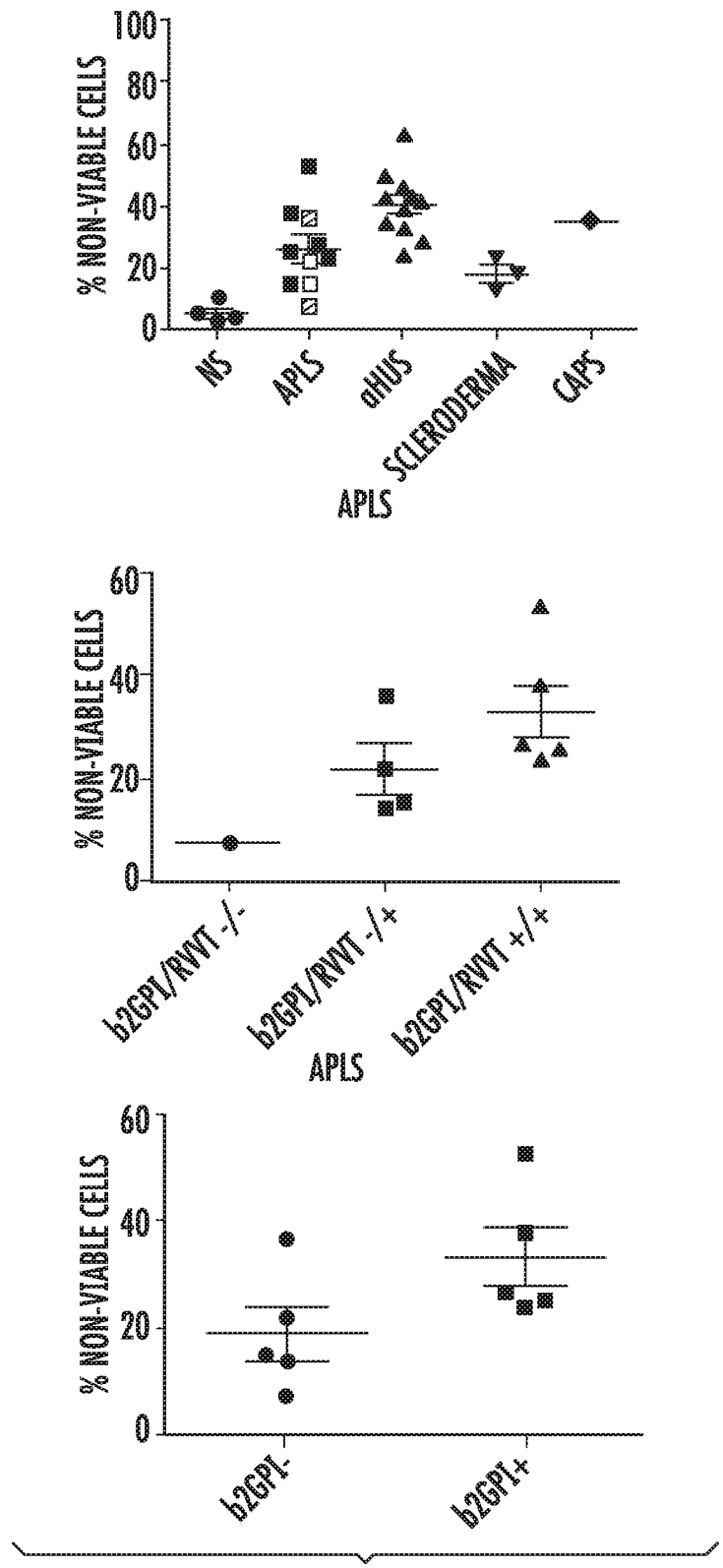
FIG. 7. WST-1 viability assay results on TF-1 cells among different disease entities.
Figure 8:
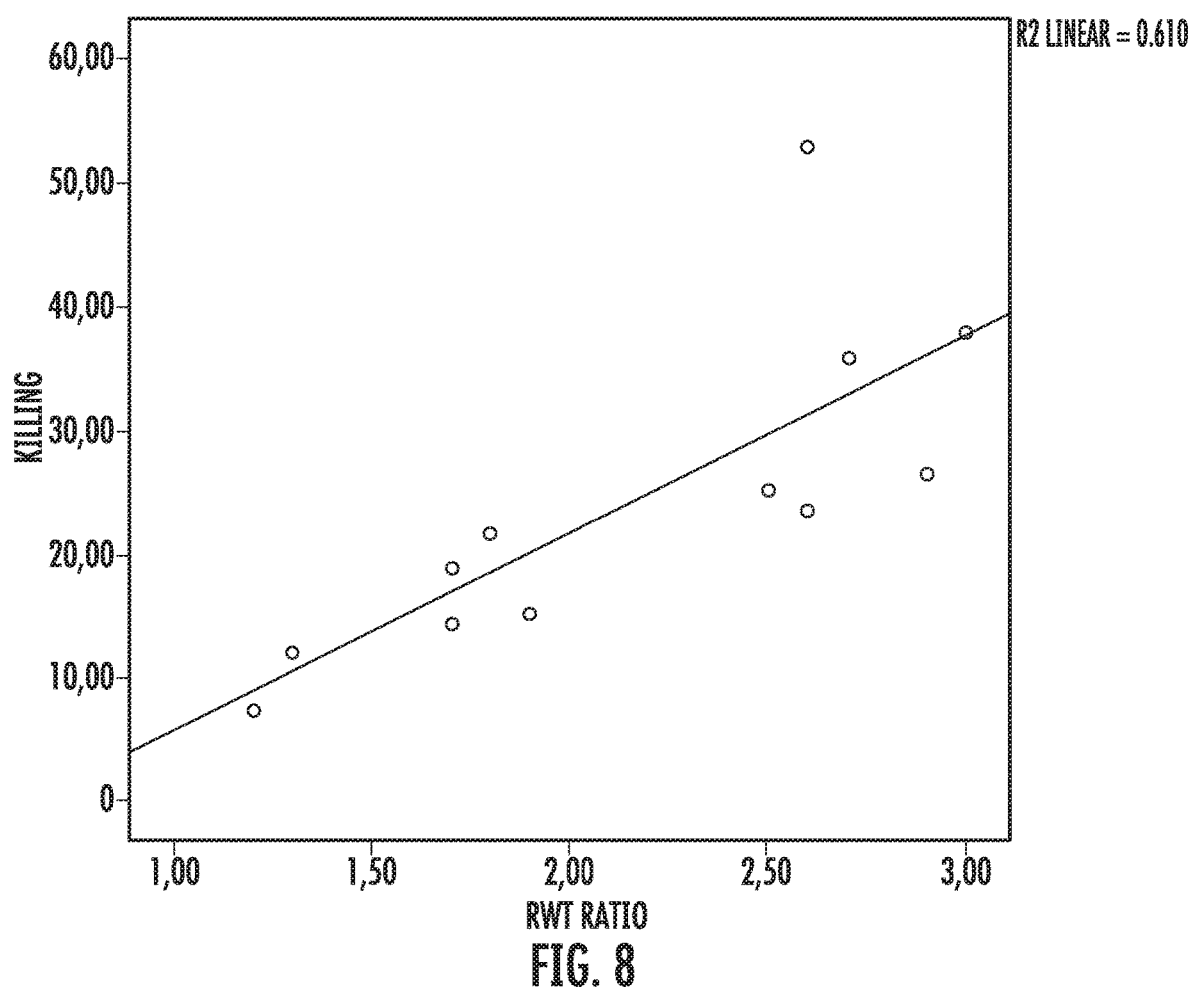
FIG. 8. Killing correlates with RVVT ratio (r=0.781, p=0.003) and shows a trend towards statistical significance with b2GPI levels (r=0.584, p=0.087).
Figure 9A:
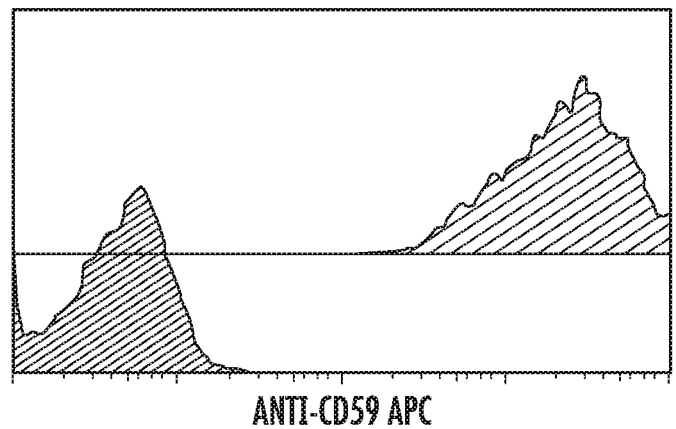
FIG. 9A-9B. Genetic disruption of PIGA in human iPS cells augments cell killing caused by complement activation.
Figure 9B:
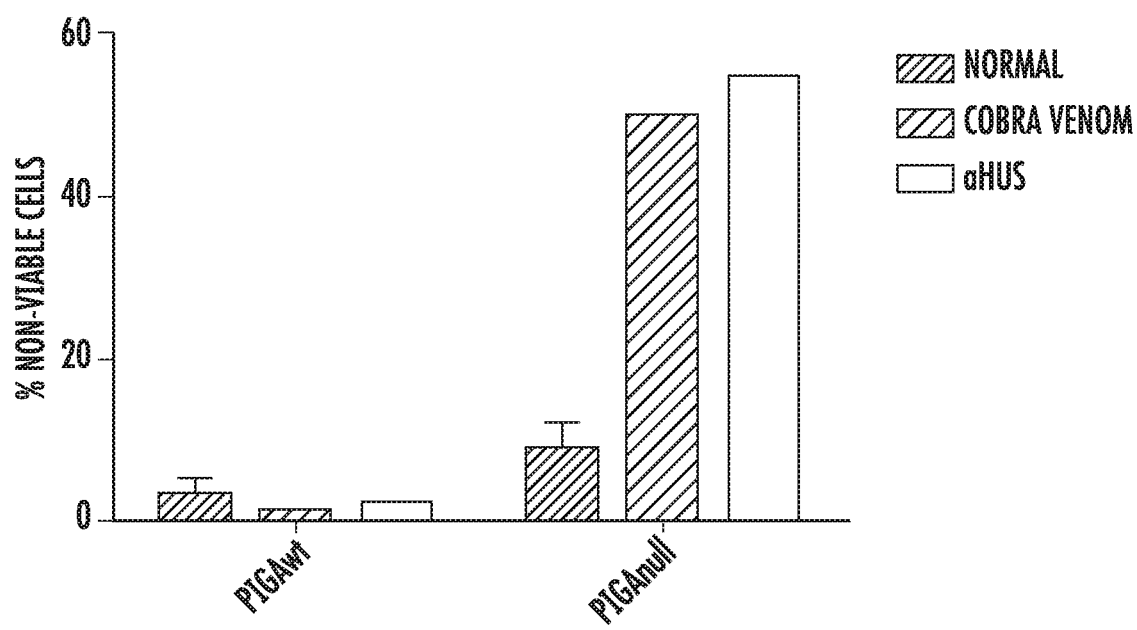

The WST-1 killing assay with PIGA null TF-1 cells was able to distinguish aHUS from healthy controls and TTP patients regardless of whether the subjects were studied at presentation, in remission on eculizumab, or in remission off eculizumab (FIG. 6A). We were initially surprised that the assay was still positive in aHUS patients on eculizumab. We hypothesized that the 1:4 serum dilution was diluting the eculizumab concentration to a level that was no longer blocking terminal complement activation. To test this hypothesis, we performed our WST-1 assay on three aHUS patients within 7 days of their next scheduled dose of eculizumab using serial serum dilutions (1:1, 1:2, 1:4, 1:8, and 1:16), as shown in FIG. 6B. Despite higher concentrations of serum as a source of complement, all three patients showed no increased killing compared to healthy controls at 1:1 dilutions; two of the three patients had no increase in killing at 1:2; and all three patients showed increased killing at 1:4 and 1:8 dilutions of their serum. There was insufficient complement in the 1:16 serum dilution in all three subjects to trigger complement-mediated killing in our assay. Lastly, to ensure that eculizumab was not somehow interfering with our assay we tested serum from a PNH patient on eculizumab and saw no increased killing in the WST-1 assay.

We next sought to determine the cutoff value that distinguishes aHUS from TTP in our WST-1 assay on PIGA null TF-1 cells. In the ROC curve analysis, a significantly high area under the curve was found (0.996, $p<0.001$). A percentage of non-viable cells higher than 21.5% was determined as a cutoff value for the diagnosis of aHUS among other TMAs with 100% sensitivity and 99% specificity. In terms of reproducibility, significantly high Lin's concordance correlation coefficient was calculated (0.923) indicating high reproducibility between tested values.

Discussion

Paroxysmal nocturnal hemoglobinuria (PNH) is a clonal hematopoietic stem cell disorder caused by a somatic PIGA mutation that leads to complement-mediated hemolysis. PIGA is required for the biosynthesis of glycosylphosphatidylinositol (GPI) biosynthesis; thus, PIGA mutant cells have a deficiency or absence of GPI anchored proteins. Two of the missing GPI-anchored proteins in PNH (CD55 and C59) are complement regulatory proteins; their deficiency explains the hemolytic anemia in PNH patients. CD55 regulates C3 convertases, and CD59 prevents the incorporation of C9 into the membrane attack complex. Thus, hemolysis in PNH is primarily due to activation of APC. Indeed, prior to 1990, the diagnosis of PNH was often based on the acidified serum test, also known as the Ham test. The principle of this assay is that PNH cells are more vulnerable to acidified serum, which serves to activate APC. Similar to aHUS, PNH is effectively treated by terminal complement inhibition.

Since most aHUS patients harbor mutations that lead to activation of APC, we hypothesized that serum from aHUS patients would kill PNH like cells more readily than serum from other TMAs such as acquired TTP or typical HUS (Shiga toxin). Here, we demonstrate a simple and rapid, serum-based assay that can differentiate aHUS from other TMAs.

One aspect of the present invention describes a reproducible, sensitive and specific cell viability assay that helps to differentiate aHUS from other TMAs, irrespective of disease status (acute phase or remission, on or off therapy with terminal complement inhibition). In PNH there is a genetic mutation, PIGA, that causes a loss of complement regulatory proteins (CD55 and CD59) on PNH blood cells. Acidifying human serum activates APC and leads to specific lysis of PNH erythrocytes because they are unable to protect themselves from the activated complement in acidified serum. In most aHUS cases there are genetic mutations that lead to activation of APC in the patient's serum. Thus, when PNH-like reagent cells (PIPLC-treated endothelial cells or PIGA null TF-1 cells) are incubated aHUS serum they rapidly accumulate C5b-9 and undergo cell death within 30 minutes in a WST-1 viability assay. This novel assay helps to distinguish aHUS and TTP.

Tests that reliably, rapidly, and affordably distinguish aHUS and TTP are highly desirable given the severe morbidity and mortality associated with these diseases and the potential cost of choosing the wrong therapy (eculizumab versus plasma exchange). Currently, aHUS is predominantly a diagnosis of exclusion once typical HUS (Shiga toxin) and TTP (ADAMTS13 activity <10%) have been excluded. The most reliable assay to distinguish between these diseases is ADAMTS13 activity. Severe TTP is usually associated with <10% of plasma ADAMTS-13. For that reason, ADAMTS13 activity higher than 10% in everyday clinical practice or even 5% in clinical trials is considered suggestive of aHUS diagnosis. However, partial ADAMTS13 deficiency may also be observed in aHUS patients with a heterozygous mutation in the ADAMTS13 gene.

Complement components C5a and C5b-9 have been reported to be elevated in plasma of patients clinically characterized as aHUS before treatment, as compared to ADAMTS13-deficient TTP patients. However, values often overlap between the two groups and no cutoff value has been determined. In addition, increased plasma levels of C3b/c, convertase C3bBbP and C5b-9 were also documented in aHUS in the acute phase as compared to remission. In an effort to develop an in vitro diagnostic assay Noris et al. have investigated C5b-9 deposition on ADP-activated endothelial cells by confocal microscopy. In agreement with our data, increased C5b-9 deposition was found in aHUS patients in acute phase and in remission as compared to normal controls. These authors also noted increased C5b-9 deposition in unaffected mutation carriers. In contrast to our data, Noris et al. were not able to detect a difference between healthy controls and aHUS patients on eculizumab therapy (Noris et al., 123(100 BLOOD 1715-26 (2014). Our assay can readily detect aHUS even in patients on eculizumab.

Approximately 50 to 60% of aHUS patients have known mutations in genes that either regulate or activate the APC, including complement factor H (CFH) and CFH-related proteins, complement factor I (CFI), CD46 (membrane cofactor protein, MCP), complement factor B, complement component C3, thrombomodulin, plasminogen, diacylglycerolkinase-ε (DGKE), and autoantibodies to CFH. Historically, penetrance of aHUS in patients with germline mutations has been estimated at 50%. A recent study has also revealed that penetrance is much lower in mutation positive relatives regardless of the gene or patient age. Therefore, genetic modifiers and environmental factors ("triggers") are considered crucial for aHUS manifestation (two-hit hypothesis).

Our invention is in agreement with the two-hit hypothesis showing that increased complement activation is evident not only in acute phase but also in remission when the second trigger can no longer be detected. We were also able to detect complement activation in the serum of aHUS patients on eculizumab. This is likely due to the fact that the concentration of eculizumab in serum diluted 1:4 is unable to block terminal complement. Indeed, killing was almost completely abrogated in serum diluted 1:1 and 1:2 suggesting that the WST-1 assay may be useful in titrating the most appropriate dose of eculizumab for aHUS patients. Our data also suggest that prompt recognition and treatment of aHUS may allow for discontinuation of eculizumab in a subset of patients as long as they are closely monitored for relapse analogous to withdrawing plasma exchange in patients with TTP that achieve remission. Indeed, four patients (1, 5, 6 and 8) have had their eculizumab treatment discontinued and remain in clinical remission for a median of 31 weeks (range, 8-60).

Our data clearly show that GPI anchor deficient reagent cell lines are especially sensitive to serum from patients with aHUS. In terms of a diagnostic assay, the cell viability assay presented here overcomes existing diagnostic difficulties and displays several advantages that render it useful in everyday clinical settings. It is an easy-to-perform, low cost assay of short duration that does not require specialized technical experience or equipment. Furthermore, it displays excellent sensitivity, specificity and reproducibility in differentiating aHUS from other TMAs.

Thus, the present invention describes an assay with high reproducibility, sensitivity and specificity in differentiating aHUS from other TMAs, based on complement-mediated apoptosis and death in GPI-AP deficient cells. Favorable outcomes of eculizumab treatment in aHUS patients underscore the importance of this diagnostic assay in implementing treatment decisions. In an era of intense efforts in personalizing medicine, our assay presents a promising tool to differentiate patients with increased complement activation that would benefit most from complement inhibitors.

Example 2: Assay for Antiphospholipid Antibody Syndrome (APS)

APS and CAPS (catastrophic APS) are poorly defined autoimmune diseases that lead to venous and arterial thrombosis, obstetric complications, and death. Currently, the diagnosis of APS is cumbersome and subject to debate as to the most appropriate diagnostic assays. Furthermore the natural history of APS and the best approach to therapy is also unclear, in part, due to variability and reliability of the various assays; thus, more reliable and specific markers for APS are needed. Here we describe a novel serum-based assay that helps to diagnose increased activity in the alternative pathway of complement, a hallmark of APS.

Antiphospholipid syndrome (APS) is an autoimmune disorder characterized by thrombosis and/or specific adverse obstetric outcomes in conjunction with antiphospholipid antibodies. Current laboratory diagnosis of APS requires the presence of a lupus anticoagulant (LA), moderate-to-high level IgG and or IgM antibodies to beta-2 glycoprotein I (B2GPI), or cardiolipin (CL) in association with specific clinical manifestations of thrombosis (arterial and/or venous) and/or pregnancy related morbidity. Patients are defined as having APS if they have 1 or more thrombotic events and have a positive antiphospholipid antibody test on more than 1 occasion at least 12 weeks apart. Catastrophic antiphospholipid syndrome (CAPS) is a highly aggressive form of APS characterized by the presence of microangiopathy and widespread thrombosis. CAPS must be distinguished from other microangiopathic conditions associated with thrombosis such as atypical hemolytic uremic syndrome (aHUS) and thrombotic thrombocytopenic purpura (TTP) that often have a similar clinical presentation. Complement is involved in the biological effect of anti-B2GPI as demonstrated by its ability to promote in vitro and in vivo complement deposition and the failure to induce vascular thrombosis in C6-deficient rats and fetal loss in C5-depleted mice. More recent data suggest that B2GPI, the major target in APS, regulates complement through its interaction with complement factor H, a serum regulator of the alternative pathway of complement. Moreover, there are successful case reports of using the C5 monoclonal antibody, eculizumab, to treat CAPS. We have developed a novel assay that is highly sensitive and specific for activation of the alternative pathway of complement. Here, we show that APS is associated with activation of the alternative pathway of complement and that activity correlates highly with the strength of the LA and the presence of antibodies to B2GPI.

Here, we report on the methods for an inexpensive, rapid, diagnostic assay to measure the complement activation and to help with the diagnosis of APS and CAPS. We previously established a PIGA mutant cell line derived from TF1 cells. PIGA is a gene required for the first step in the biosynthesis of glycosylphosphatidylinositol (GPI), a lipid moiety that anchors dozens of proteins to the cell surface. Two of the GPI-anchored proteins that are defective in the TF1 cell line are CD55 and CD59. The proteins both regulate complement. CD55 blocks C3 convertases and CD59 interferes blocks terminal complement activation. Our new technology uses this cell line a reporter cell line for activation of complement in patient serum. Briefly, we collect 5 cc of serum from patients, dilute it 1:4 with growth medium and measure viability of the PIGA mutant TF1 cells after 30 minutes using a WST1 assay. To confirm that the cell kill is associated with complement we stain the cells with a monoclonal antibody to C5b9 (terminal complement attack) and assay the staining by flow cytometry.

Materials and Methods

Sample Collection.

Blood is collected in serum separation tubes and is immediately centrifuged at 4° C. Serum is separated and stored at −80° C. Heat inactivation is performed the same day of the experiment, incubating the serum at 56° C. for 30 minutes.

Cell Viability Assay.

The assay is performed on a glycosylphosphatidylinositol-anchored proteins (GPI-AP) deficient TF-1 cell line. Cells are maintained in RPMI 1640 medium supplemented with 2 ng/mL GM-CSF, 2 mM 1-glutamine, penicillin/streptomycin, and 10% fetal calf serum under BL2 lab containment.

Cells are plated in a U-shaped 96-well plate at a density of approximately 4,000 cells/well and cultured until confluent. Then, cells are washed with PBS and incubated with serum at a concentration of 1:4 for 30 minutes at 37° C. Serum is diluted in GVB (gelatin veronal buffer, Sigma). Cells are washed again with PBS and incubated with the cell proliferation reagent (4-[3-(4-Iodophenyl)-2-(4-nitrophenyl)-2H-5-tetrazolio]-1.3-benzene disulfonate/WST-1, Roche) for 3 hours at 37° C. Wst-1 is diluted in the cell culture medium at a concentration of 1:10 and 100 µl of Wst-1 solution is added per well. Absorbance is measured in a microplate (ELISA) reader at 450 nm with a reference wavelength at 650 nm, according to the manufacturer's instructions and previous publication. The colorimetric assay is based on cleavage of the tetrazolium salt, WST-1, by mitochondrial dehydrogenases in viable cells.

Data Analysis.

Absorbance values of each sample are normalized after subtraction of the absorbance value of a blank cell. Percentage of viable cells is expressed as a ratio of the absorbance of each sample multiplied by 100, to the absorbance of the same sample's heat-inactivated control. Percentage of dead cells is calculated after subtracting percentage of viable cells from 100.

Example 3: Modified Ham Test Protocol

Sample Collection.

Serum should be collected as soon as possible after the blood is drawn and stored at −80° C. within 4 hours.

Equipment needed.

TF-1 PIGA null cells cultured in RPMI 1640 medium supplemented with 2 ng/mL of granulocyte-macrophage colony-stimulating factor (GM-CSF), 2 mM 1-glutamine, penicillin/streptomycin, and 10% fetal calf serum.

U-shaped 96-well plate

Gelatin veronal buffer (GVB, Sigma-Aldrich)

Negative control: normal human AB serum

Positive control: a) cobra venom factor (CVF, Complement technology), or b) serum from aHUS patient WST-1 Assay (Roche)

Absorbance reader

Preparation.

Calculate the number of wells needed. Each sample and its heat-inactivated control are analyzed in triplicates. Each assay has a negative control (normal serum and heat-inactivated normal serum) and a positive control.

Collect desired number of TF-1 PIGA null cells (according to the number of wells −4,000 cells/well) from culture.

Wash cells with PBS and re-suspend in the desired volume (according to the number of wells—100 µl/well) with their culture medium (RPMI).

Plate cells in U-shaped 96-well plates (100 µl/well) and culture overnight.

Assay.

Dilute samples and controls in GVB. Standard amount of serum used is 20%. Preparations should be done on ice.

If CVF is used as a positive control, add 13% of CVF for 20% of normal serum in GVB. Pre-incubate for 15 minutes at 37° C.

Add 100 µl of PBS/well in the 96-well plate.

Spin down (1000 g for 5 minutes) and carefully aspirate the supernatant.

Add 100 µl of samples and control/well and incubate for 30 minutes at 37° C.

Wash cells again with 100 µl PBS.

Spin down (1000 g for 5 minutes) and carefully aspirate the supernatant.

Dilute WST-1 in RPMI (10 µl WST in a total 100 µl/well). Add the WST-1 solution to three additional empty wells that will contain only the WST-1 and serve as blank wells.

Incubate for 2 hours at 37° C.

Read absorbance at 490 nm with a reference wavelength at 595 nm.

Data Analysis.

Calculate the mean absorbance of each sample. Subtract the mean absorbance value of the blank cells from each sample's mean absorbance. Calculate percentage of non-viable cells was calculated using the following formula: 100−(mean sample's absorbance*100/heat-inactivated sample's absorbance).

Example 4: Modified Ham Test Distinguishes aHUS from TTP and Predicts Response to Eculizumab Introduction.

Atypical hemolytic uremic syndrome (aHUS) is a disease of excessive alternative pathway of complement (APC) activation that can be treated with eculizumab. Clinicians have been hesitant to administer eculizumab because of the lack of a diagnostic assay for aHUS and the expense of the drug. Mutations in genes that regulate the APC (factor H/CFH, I/CFI, CD46, etc.) underlie up to 50% of aHUS patients, but the clinical relevance of these mutations is often unclear. We developed the modified Ham test to distinguish aHUS from thrombotic thrombocytopenic purpura (TTP). This functional assay measures cell viability (WST-1) of a PIGA mutant cell line following exposure to patient serum. The cells are more sensitive to APC killing because complement regulators CD55 and CD59 are absent from the cell surface. CD46 is a transmembrane APC regulator that remains on the surface of the PIGA-null TF1 cells. Here, we show that the modified Ham test predicts response to eculizumab and can be adapted to assess the contribution of APC mutations to clinical phenotype.

Method.

We studied adult patients with thrombotic microangiopathies (TMA) who presented to our hospital from July 2014 through June 2015 and two patients from outside institutions. aHUS was defined by the presence of a TMA with platelet count $<100\times10^9$/L, serum creatinine >2.25 mg/dL, and ADAMTS13 activity >10%. TTP was defined as TMA in association with an ADAMTS13≤10%. Response to eculizumab was defined as TMA event-free status for at least 12 weeks and normalization of hematologic values. The modified Ham test was performed utilizing PIGA-null myeloid TF1 (PIGA only knockout/KO) as previously described. We additionally knocked-out CD46/membrane cofactor protein (MCP) gene in the PIGA-null TF-1 cell line (PIGA/CD46 double KO), and wild-type TF1 cells (CD46 only KO) using CRISPR/Cas9 technology.

Results.

Figure 10A:
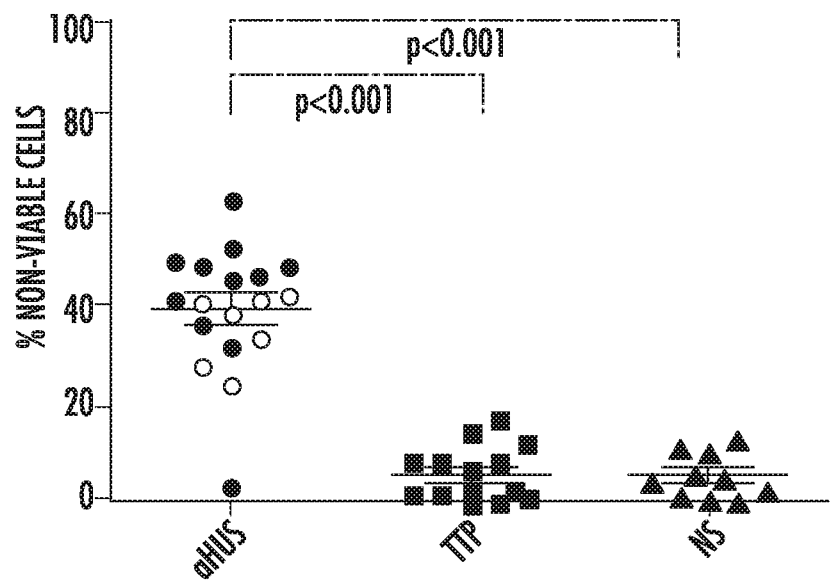
FIG. 10A. The modified Ham test was performed using PIGA-null TF1 reagent cells with 37 serum samples from 29 patients with TMAs. 13 patients were diagnosed with aHUS, 15 with TTP, and 1 with TMA of unknown etiology. APC-mediated cell killing was significantly increased in patients with aHUS compared to TTP (grey shapes symbolize patients on eculizumab).

The modified Ham test was performed using PIGA-null TF1 reagent cells with 37 serum samples from 29 patients with TMAs. 13 patients were diagnosed with aHUS, 15 with TTP, and 1 with TMA of unknown etiology. APC-mediated cell killing was significantly increased in patients with aHUS compared to TTP (FIG. 10A, grey shapes symbolize patients on eculizumab). In the ROC analysis, the cut-off value of 20.5% killing suggests an aHUS diagnosis with 100% specificity and 94.1% sensitivity. One patient presented with a TMA of unknown etiology (normal ADAMTS13 levels, and did not satisfy criteria for aHUS due to a creatinine of <1.3; no known complement-related mutations or autoantibodies were detected). The patient showed no increased killing with the modified Ham test and had a transient response to plasma exchange and eculizumab but relapsed after 8 weeks of eculizumab treatment.

12 aHUS patients received eculizumab and all responded to treatment. Eculizumab was discontinued in 6 patients after a median 11 doses (range 5-37) and all remain in remission for 8 months (range 4-15). The modified Ham test was positive in all aHUS patients that responded to eculizumab (positive predictive value 100%) and negative in 1 responder with a heterozygous variant of unknown significance in DGKE. Among 12 patients with aHUS, 7 patients had mutations in genes previously associated with aHUS (3 CFH, 1 DGKE, 1 CFH and CD46, 1 CFH and ADAMTS13, and 1 CFH and thrombomodulin). Six of those patients had additional heterozygous deletions in the CFHR3-CFHR1 gene region.

Figure 10B:
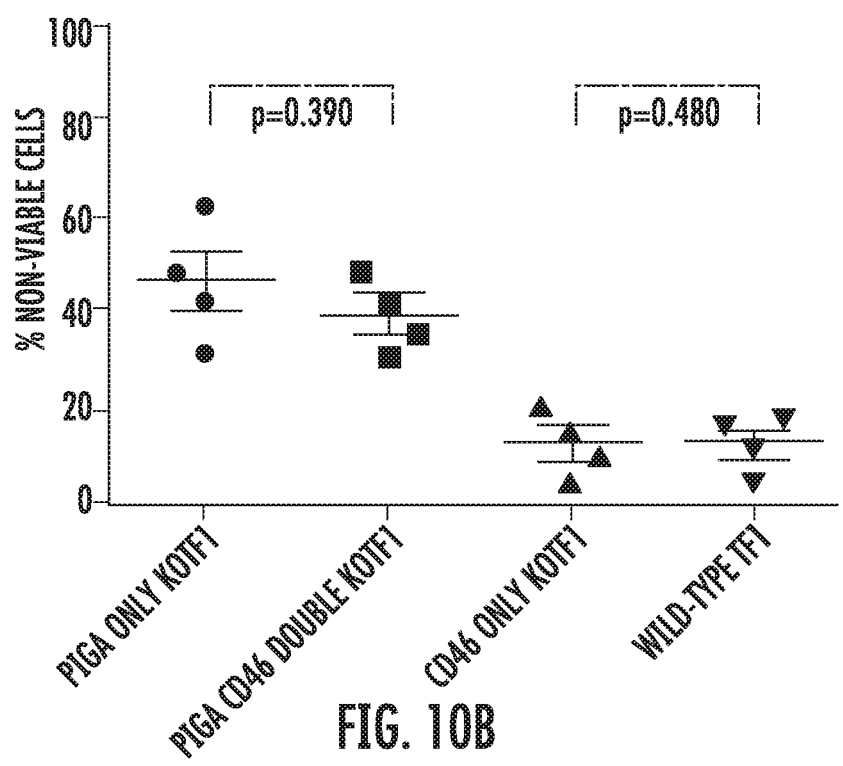
FIG. 10B. To study the impact of CD46 insufficiency on complement regulation we exposed PIGA/CD46 double KO TF1, and CD46 only KO lines to aHUS serum and measured cell viability in the modified Ham test. The CD46 KO line was no more susceptible to killing than wild-type TF1 cells and the PIGA/CD46 double KO cells were no more sensitive to killing than the PIGA only KO cells, suggesting that CD46 is a weak complement regulator compared to the combination of CD55 and CD59.
Figure 11A:
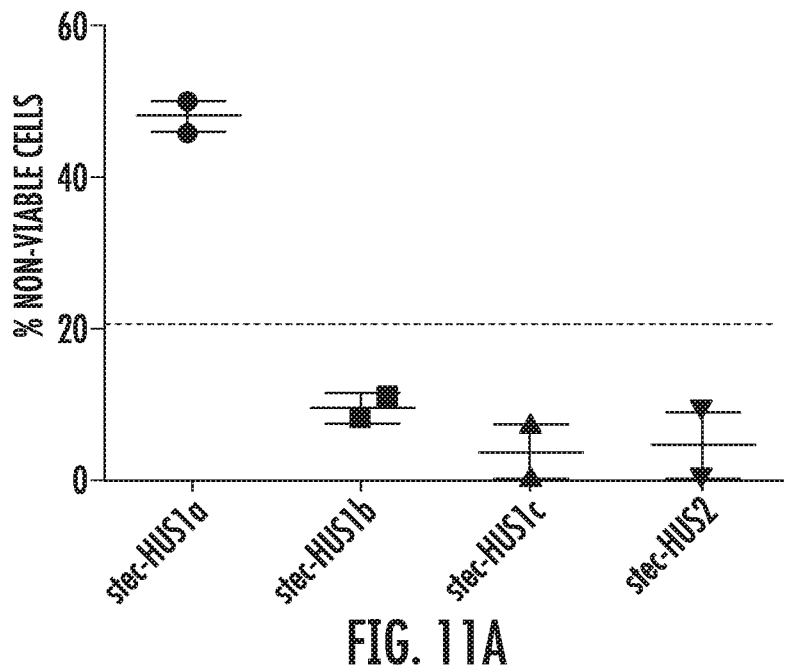
FIG. 11A-11C. Complement activation in Shiga-toxin associated HUS.
Figure 11B:
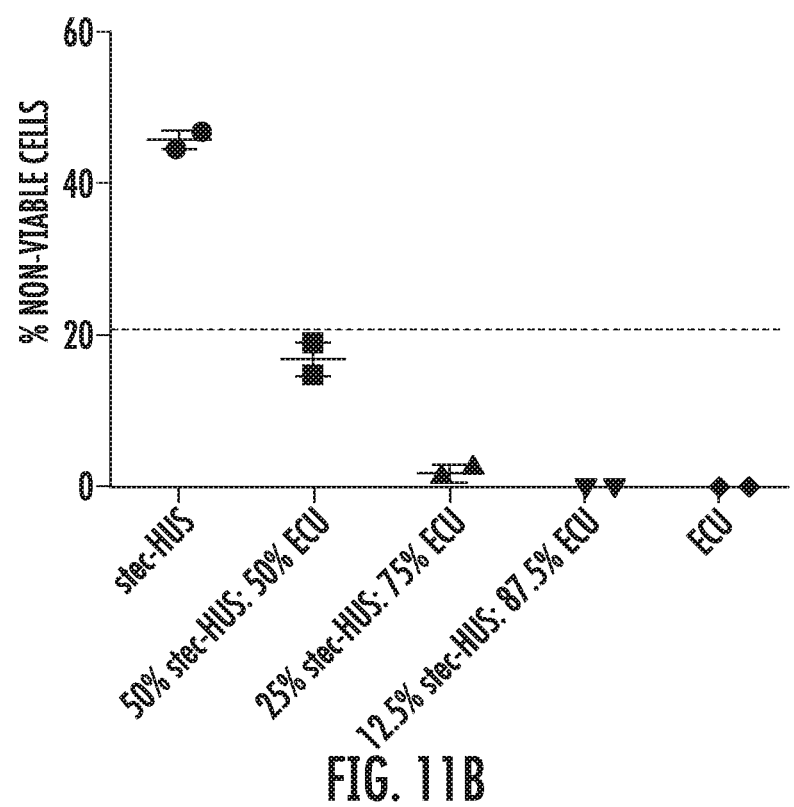
Figure 11C:
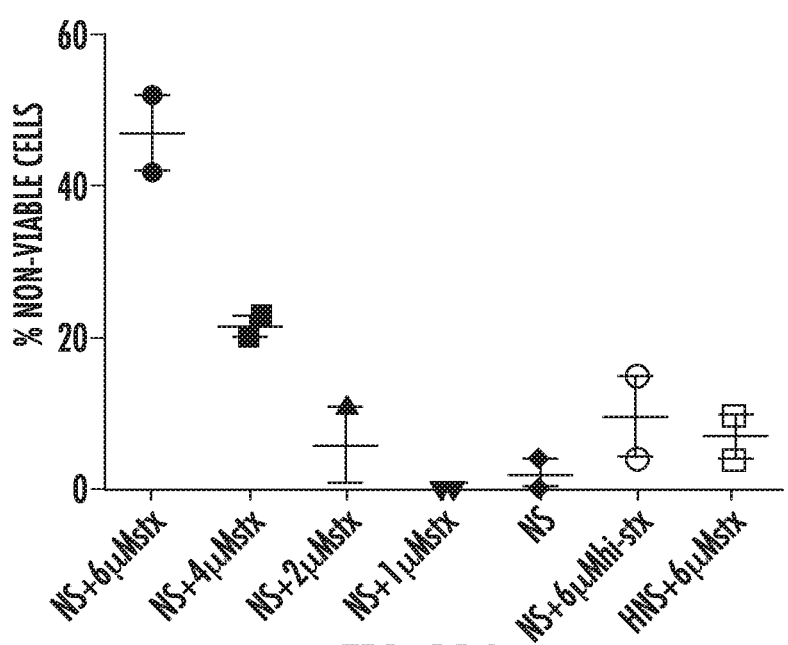

To study the impact of CD46 insufficiency on complement regulation we exposed PIGA/CD46 double KO TF1, and CD46 only KO lines to aHUS serum and measured cell viability in the modified Ham test. The CD46 KO line was no more susceptible to killing than wild-type TF1 cells and the PIGA/CD46 double KO cells were no more sensitive to killing than the PIGA only KO cells, suggesting that CD46 is a weak complement regulator compared to the combination of CD55 and CD59 (FIG. 10B).

Conclusions.

The modified Ham test reliably distinguishes most forms of aHUS from TTP and predicts response to eculizumab. Mutations in CD46 do not impact susceptibility to APC killing in the modified Ham test. The modified Ham test may be adapted to inform investigators and clinicians on the correlation between genotype and phenotype.

Example 5: Direct Evidence of Complement Activation in HELLP Syndrome: A Link to Atypical Hemolytic Uremic Syndrome Objective.

Although HELLP syndrome (hemolysis, elevated liver enzymes, and low platelets) has been long recognized as a severe variant of preeclampsia, its pathogenesis remains unclear. Recent evidence and clinical similarities suggest a link to atypical hemolytic uremic syndrome (aHUS), a disease of excessive complement activation through the alternative complement pathway (APC). To test this hypothesis we utilized a functional complement assay, the modified Ham test recently described for aHUS diagnosis.

Methods.

Sera from women with normal pregnancies, preeclampsia with severe features, and women diagnosed with classic HELLP and atypical HELLP were tested for complement activation markers: serum C5b-9 levels and the modified Ham test.

Results.

9 sera of women with classic or atypical HELLP, 7 of women with preeclampsia with severe features, and 11 controls were tested. We found no significant difference in serum C5b-9 levels (p=0.808). However, increased complement activation represented as significantly higher percentage of cell killing (25.7±19.8% versus 4.1±7.3%, p=0.005) was found in participants with classic or atypical HELLP compared to participants with normal pregnancy. Classic HELLP demonstrated significant difference in cell killing when compared to severe preeclampsia (38.7+9.8% versus 13.0+11.7, p=0.048). Mixing HELLP serum with eculizumab containing serum resulted in a significant decrease of cell killing compared to HELLP serum alone (p=0.007).

Conclusion.

Classic and atypical HELLP syndrome is pathogenetically related to increased complement activation through the APC pathway demonstrated by a rapid and inexpensive assay, the modified Ham test. This test may be a promising tool to identify patients that would benefit from complement inhibition by eculizumab.

Introduction

Preeclampsia is a multisystem disorder of pregnancy which manifests as hypertension, proteinuria, and/or other end organ damage as a result of endothelial dysfunction, and occurs in 3-5% of all pregnancies. HELLP syndrome (hemolysis, elevated liver enzymes, and low platelets) is a severe variant of preeclampsia. First defined by Weinstein in 1982, HELLP syndrome has a reported incidence of up to 0.8% of all pregnancies. Although there are no strict criteria for its diagnosis, the Tennessee and Mississippi classifications have been proposed using platelet count, lactate dehydrogenase (LDH) levels, bilirubin and aspartate aminotransferase (AST) with or without alanine aminotransferase (ALT) levels (FIG. 12). However, many women with preeclampsia may have abnormalities such as isolated thrombocytopenia or elevated liver enzymes without the classic HELLP syndrome. These women are usually considered "impending," "partial", "incomplete" or "atypical" HELLP.

HELLP may result in severe morbidity and mortality to both the mother and fetus. DIC is the most frequent severe maternal complication followed by hepatic rupture and bleeding. Delivery is the treatment of choice, but early delivery may have severe consequences to the neonate. Neonatal mortality and morbidity are significantly higher if the fetus is delivered before 34 weeks. Treatment of HELLP prior to delivery is largely supportive and consists of steroids to increase fetal lung maturity, magnesium for maternal seizure prophylaxis, and management of hypertension.

While HELLP is traditionally thought to be within the spectrum of preeclampsia, recent evidence implicates complement activation in HELLP pathogenesis. Prior studies have postulated an up-regulation of the alternative complement pathway (APC) using markers in serum and urine (C5b-9 or membrane attack complex/MAC). Recently, germline mutations in the APC have been found in up to 20% of HELLP patients. Similar mutations are also found in atypical hemolytic uremic syndrome (aHUS), a disease of excess APC activation caused by inherited or acquired defects in the regulation of APC. Indeed, mothers with HELLP have manifestations very similar to aHUS which mainly involve microangiopathic hemolytic anemia (MAHA), thrombocytopenia, thrombotic microangiopathy, renal dysfunction, hypertension, seizures and altered mental status. Unlike HELLP, where the mainstay of therapy is limited to supportive care, expectant management and ultimately delivery, aHUS is treated with a C5 monoclonal antibody, eculizumab. This therapy is highly effective and is now considered the treatment of choice for aHUS. Eculizumab treatment has been also recently described in a case report of a HELLP patient with favorable effects.

Therefore, we hypothesized that women with atypical HELLP and classical HELLP syndrome may have increased APC activation similar to aHUS that can be favorably reduced by complement inhibition in vitro. To test this hypothesis we used the modified Ham test which has been recently described to reliably detect increased APC activation in aHUS.

Methods and Materials

Study Population.

We performed an observational, case-controlled study of women with classic HELLP (Group 1), atypical HELLP (Group 2), preeclampsia with severe features (Group 3), and women with normal pregnancies (Group 4). All participants were greater than 23 weeks pregnant. Preeclampsia with severe features was defined by the ACOG executive summary on hypertension in pregnancy. Classic HELLP syndrome was defined satisfying all Mississippi or Tennessee criteria for HELLP syndrome. The investigators defined atypical HELLP as having at least one laboratory abnormality found in the Mississippi or Tennessee criteria for HELLP syndrome. Groups 1, 2, and 3 were recruited antenatally from the Johns Hopkins Hospital and Johns Hopkins Bayview Medical Center from Sep. 1, 2014 to May 31, 2015, and Group 4 was recruited from the institution's outpatient centers. Women with known sickle cell disease, systemic lupus erythematous, antiphospholipid antibody syndrome, or previous diagnosed microangiopathic and hemolytic diseases were excluded from all four groups. Women with any hypertensive diseases of pregnancy were excluded from Group 4. All participants gave written informed consent, and the study was approved by the Johns Hopkins University Institutional Review Board.

Blood from Groups 1, 2, and 3 were collected at the time of admission and diagnosis, and blood from Group 4 was collected in the outpatient setting. The blood from all four groups was collected in serum separation tubes and was centrifuged at 4° C. Serum was separated and stored at −80° C. Samples were processed and stored within 4 hours after the blood was drawn to prevent ex vivo complement activation. Coded samples were sent de-identified in the laboratory for further testing. Eculizumab containing serum was drawn following informed consent from a PNH patient within 60 minutes of eculizumab infusion.

Serum C5b-9 Levels.

Serum C5b-9 levels were determined using a commercially available ELISA (enzyme-linked immunosorbent assay) kit (Quidel, San Diego, Calif.).

Modified Ham Test.

The modified Ham test was performed as previously described16. Briefly, PNH-like reagent cells (PIGA-null TF-1 cell line) previously established in our laboratory were used 17. PIGA-null TF-1 cells were plated in U-shaped 96-well plates at a density of 4,000 cells/well and cultured until confluent. Then, cells were washed with PBS and incubated with 20% of serum in GVB in triplicates for 30 minutes at 37° C. Cells were washed again with PBS and incubated with the cell proliferation reagent 4-[3-(4-Iodophenyl)-2-(4-nitrophenyl)-2H-5-tetrazolio]-1.3-benzene disulfonate/WST-1 (Roche, Switzerland) for 2 hours at 37° C. WST-1 was diluted in the cell culture medium at a concentration of 1:10 and 100 µl of WST-1 solution was added per well. Absorbance was measured in an iMark Microplate Absorbance Reader (Bio-rad, Hercules, Calif.) at 490 nm with a reference wavelength at 595 nm.

Heat-inactivated serum was used as a negative control. Heat inactivation was performed the same day of the experiment, incubating the serum at 56° C. for 30 minutes. Normal human AB serum (H4522, Sigma-Aldrich, St. Louis, Mo.) was used as an internal control of the assay. Absorbance values of each sample were normalized after subtraction of the absorbance value of a blank cell (WST-1 solution). Percentage of viable cells was expressed as a ratio of the absorbance of each sample multiplied by 100, to the absorbance of the same sample's heat-inactivated control. Thus, percentage of non-viable cells (cell killing) was calculated using the following formula: 100−(sample absorbance*100/heat189 inactivated sample's absorbance). Assay validation studies have indicated that sample storage at room temperature for more than 4 hours or overnight in a refrigerator results in higher than 50% reduction of cell killing in the modified Ham test. Results are not affected by one cycle of sample freeze/thaw at −80° C. if all preparations are made on ice.

In Vitro Evaluation of Complement Inhibition.

Complement inhibition in vitro was also evaluated using the modified Ham test. Eculizumab containing serum from a PNH patient was mixed at different ratios with HELLP sera (50-50%, 25-75% and 12.5-87.5% of HELLP and ECU sera respectively). Total amount of serum in the assay remained unchanged (20%).

Statistical Analysis.

Statistical analysis was performed using the Statistical Package for Social Sciences (SPSS) 20.0 for Windows (SPSS, Chicago, Ill.). The independent samples Student t test was used to compare differences between the mean values of two groups. One-way ANOVA with Bonferroni's correction or nonparametric tests were used to compare means between more than two groups. Receiver operating characteristic (ROC) curve analysis was performed to determine the cut-off value, sensitivity and specificity of HELLP diagnosis by the modified Ham test. A p-value ≤0.05 was considered statistically significant. Statistical power analysis was performed retrospectively calculating the observed power in a univariate analysis model.

Results

Study Population.

We studied a total of 9 sera from women with classic HELLP (Group 1) and atypical HELLP syndrome (Group 2), 7 sera from women with preeclampsia with severe features (Group 3), and 11 control sera of women with normal pregnancies (Group 4). Age was similar among groups (27.4±3.8 versus 26.3±5.4 and 28.6±5.0 respectively, p=0.596). Laboratory and clinical characteristics of participants in Groups 1, 2, and 3 are shown in FIG. 13. Two participants studied antepartum with preeclampsia with severe features but not HELLP, were also evaluated postpartum when they were diagnosed with classic HELLP and atypical HELLP.

Serum C5b-9 Levels.

Figure 14:
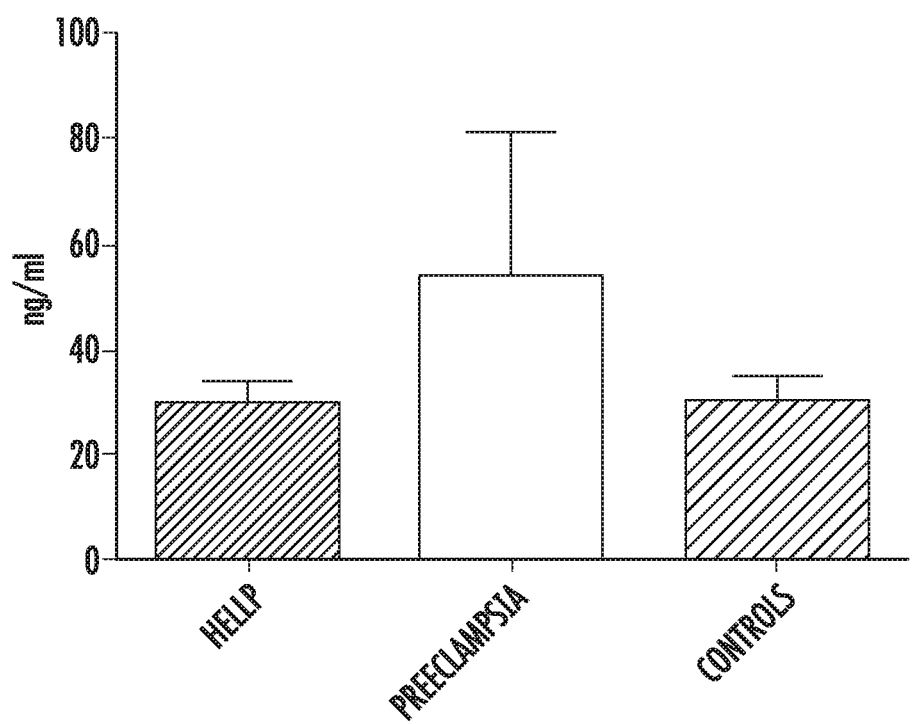
FIG. 14. Serum C5b-9 levels patients with preeclampsia with severe features with and without HELLP and normal controls No significant difference was found among the three groups (p=0.808).

We first studied C5b-9 (membrane attack complex) levels as a biomarker of terminal complement activation. C5b-9 is the terminal product of the complement cascade that lands on the cell membrane inducing complement-mediated cell killing. Although C5b-9 has been found increased in diseases with excess complement activation such as aHUS, their levels significantly overlap with diseases not characterized by systemic complement activation. In the present study we found no significant difference in serum C5b-9 levels among participants with preeclampsia with severe features with and without HELLP and normal controls (p=0.808), as shown in FIG. 14.

Modified Ham Test.

Figure 15A:
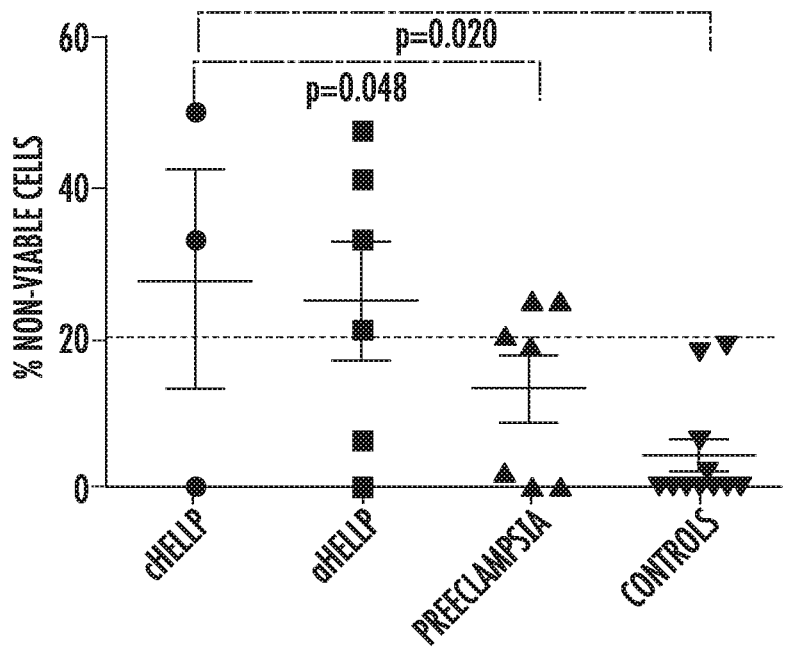
FIG. 15A-15B. Modified Ham test in the HELLP syndrome.

We next sought to investigate complement activation in an assay that reliably distinguished systemic complement activation observed in aHUS, the modified Ham test. The modified Ham test reflects complement activation as a percentage of complement-mediated cell killing and is thereby a functional assay. Participants in Groups 1 and 2 showed significantly higher percentage of cell killing than participants with normal pregnancy when combined (25.7±19.8% versus 4.1±7.3%, p=0.005). The observed power in the univariate analysis model was 86.7%. Also, when Group 1 and 2 were separated, Group 1 showed significantly more killing than Group 3 and Group 4 (38.7±9.8% versus 13.0±11.7% and 4.1±7.3%, p=0.048 and p=0.020 respectively). Interestingly, cell killing was above the cut-off value determined for aHUS diagnosis (21.5%). In 2 out of 3 participants diagnosed with classic HELLP and 4 out of 6 participants diagnosed with atypical HELLP showed values above the cutoff. One of the 235 participants (case 3 in FIG. 13), had an increase in killing antenatally and immediately after delivery was diagnosed with classic HELLP syndrome, suggesting that she may have had a genetic predisposition to acquire HELLP. The other participant (case 4 in FIG. 13) had minimal cell killing antepartum but returned on postpartum day 4 with a HELLP syndrome and cell killing minimally above threshold value. Results are summarized in FIG. 15A.

Figure 15B:
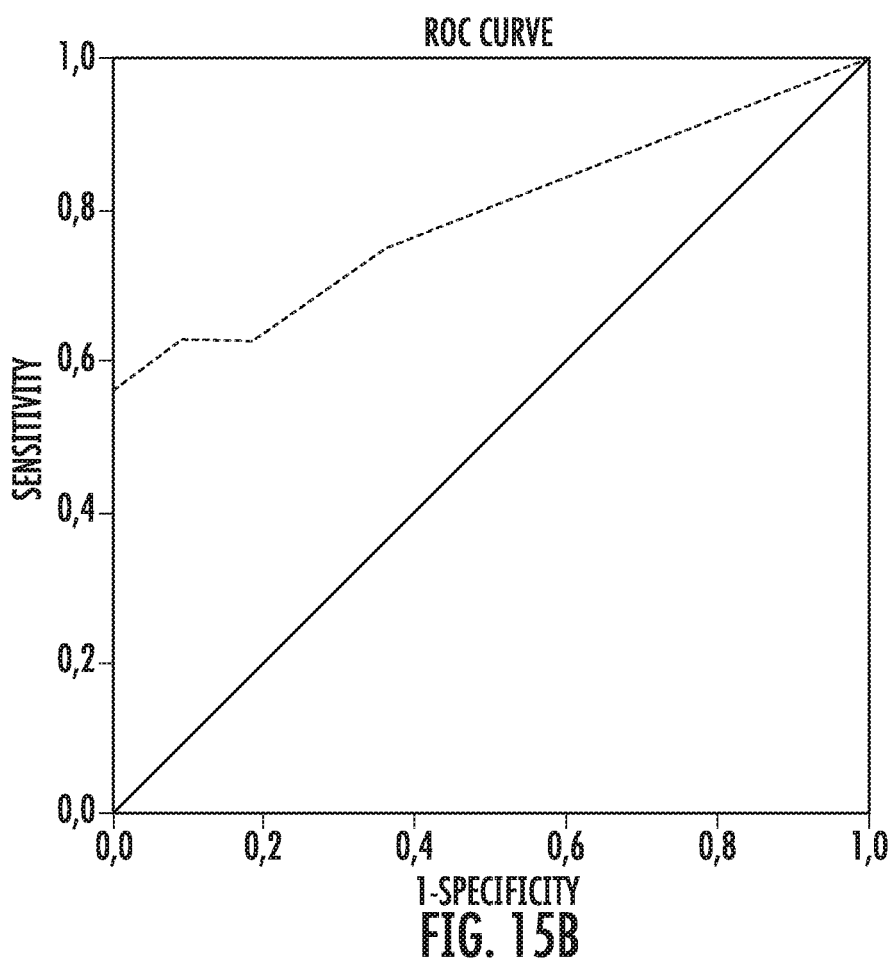

To determine a cut-off value above which the modified Ham test would be considered positive for HELLP diagnosis, we performed a ROC curve analysis that showed a significant area under the curve (area under the curve=0.781, p-value=0.019). We were able to determine a percentage of non-viable cells higher than 20.5% as the cut-off value for the diagnosis of HELLP with 66.7% sensitivity and 88.9% specificity. ROC curve is shown in FIG. 15B.

In Vitro Evaluation of Complement Inhibition.

Figure 16:
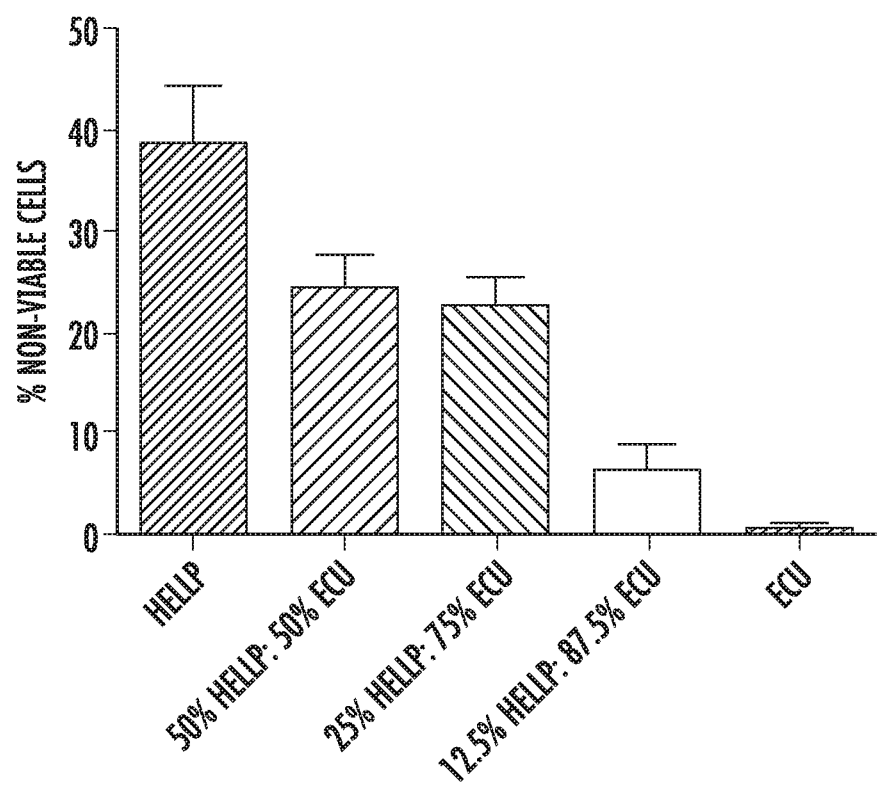
FIG. 16. Complement inhibition by anti-C5 monoclonal antibody (Eculizumab) abrogates cell killing in the modified Ham test. Serum from a PNH (paroxysmal nocturnal hemoglobinuria) patient on Eculizumab collected within 60 minutes of eculizumab infusion (ECU) was mixed with sera from four HELLP patients in different percentages (50-50%, 25-75% and 12.5-87.5% of HELLP and ECU sera respectively). Total amount of serum in the assay remained unchanged (20%). Percentage of non-viable cells was significantly lower when Eculizumab was present in the serum (p=0.007).

Eculizumab is highly effective in treating diseases of terminal complement activation such as PNH and aHUS. Therefore, we hypothesized that eculizumab would abrogate cell killing caused by HELLP serum. As expected, eculizumab-containing serum alone caused no increase in cell killing. However, mixing HELLP serum with increased cell killing with eculizumab-containing serum resulted in a significant decrease of cell killing compared to atypical HELLP sera alone (p=0.007), FIG. 16.

Discussion

The present study provides evidence that there is increased complement activation through the APC pathway in a subset of women with preeclampsia with severe features and classic or atypical HELLP syndrome. This provides evidence of a link among preeclampsia, HELLP syndrome, and diseases of excess complement activation, namely aHUS. HELLP syndrome is categorized clinically on the severe end of the spectrum of disease for preeclampsia resulting in lab abnormalities. A recognized limitation in the diagnosis of and consequently research into HELLP syndrome is that there are differently accepted criteria for both classic HELLP and atypical HELLP. In addition, LDH, AST and bilirubin are not specific for liver dysfunction and their elevation may be caused by intravascular hemolysis alone. For the purpose of this study, the investigators used both the Mississippi and Tennessee Criteria to define classic HELLP, and inclusion criterion into the atypical HELLP group was having at least one abnormality from these two criteria.

Like preeclampsia and HELLP syndrome, aHUS involves kidney injury and thrombotic microangiopathy. aHUS results from both inherited and acquired defects in the regulation of APC. Mutations in genes regulating or activating complement involve serum (such as complement factor H and I, complement component C3) and cell membrane factors (such as CD46 or membrane cofactor protein and thrombomodulin). Interestingly enough, genetic mutations are found in 50-60% of patients diagnosed with aHUS and triggers are considered crucial for the manifestation of the disease (two-hit model). Pregnancy in itself is a common trigger for aHUS, comprise 7-20% of cases, and 80% of pregnancy-associated aHUS is diagnosed in the postpartum period.

Since aHUS cannot be reliably diagnosed by genetic testing and exclusion of other thrombotic microangiopathies (TMAs), biomarkers of complement activation, such as C5b-9 levels, have been studied. Although elevated in plasma of aHUS patients before treatment, C5b-9 values often overlap between aHUS and other TMAs, such as thrombotic thrombocytopenic purpura (TTP). In effort to implement aHUS diagnosis in the non-pregnant population, we have recently described a novel, rapid, serum-based assay, the modified Ham test. This assay proved to reliably distinguish increased complement activation observed in aHUS versus other TMAs, including TTP. The principle of the assay is based on the susceptibility of a genetically modified cell line that harbors a mutation in the PIGA gene (PIGA-null TF-1 cells). The latter is responsible for glycosylphosphatidylinositol (GPI) biosynthesis and is mutated in a complement-mediated hemolytic anemia, paroxysmal nocturnal hemoglobinuria (PNH). PIGA mutant cells are susceptible to complement-mediated cell killing due to the absence of GPI anchored complement regulatory proteins (CD55 and CD59). Therefore, complement activated serum causes increased cell killing compared to normal serum in the modified Ham test.

Similar to our previous findings in the non-pregnant population, serum C5b-9 levels did not prove a reliable marker of complement activation in pregnant women with preeclampsia with severe features with or without HELLP. However, utilizing the modified Ham test we were able to show that classic and atypical HELLP sera cause increased complement-mediated cell killing to a degree similar to that of aHUS serum. Indeed, the cut-off value defined for HELLP diagnosis was 20.5% whereas the cut off value previously defined for aHUS was 21.5%. Interestingly, one participant studied both antepartum and postpartum exhibited increased cell killing both times (case 3). The other participant which was studied both antepartum and postpartum showed no significant killing in the antepartum state, but was later diagnosed with atypical HELLP and showed significantly increased killing upon postpartum readmission, albeit marginally above threshold (case 4). If these findings are validated in larger cohorts, the modified Ham test could serve not only as a diagnostic test to identify patients that would benefit from complement inhibition treatment, but also as a screening and/or biomarker tool for at-risk populations.

More importantly, we have shown that complement inhibition by eculizumab can effectively block complement-mediated cell killing demonstrated in HELLP serum with increased cell killing. This experiment is a proof-of-principle behind an already published case report of successful treatment with eculizumab. There is a long experience of effective eculizumab use in pregnant women with PNH or pregnancy-related aHUS. No adverse maternal or fetal outcomes and no complications after breast feeding have been reported and eculizumab is not detected in fetal plasma. Based upon the evidence of the present study, eculizumab treatment seems promising for patients with preeclampsia with severe features as well as classic and atypical HELLP syndrome diagnosed with early preterm fetuses. It is reasonable to hope that upon diagnosis of these diseases there can be prolonged latency of pregnancy in early preterm fetuses.

Our study has limitations. First, the modified Ham test was negative in 3 out of 9 participants with classic or atypical HELLP. Several possible explanations exist. The modified Ham test is serum-based and may not theoretically detect increased complement activation caused by mutations in cell membrane factors. Mutations in a membrane complement regulatory factor (CD46 or membrane cofactor protein) have been documented in a case report of patient with HELLP and in 4 out of 59 patients (6.8%) with preeclampsia with severe features and/or HELLP studied. Since mutations in other membrane complement regulatory factors in HELLP have not been studied yet, membrane abnormalities may account the negative results of the modified Ham test. Furthermore, one cannot rule out that other mechanisms and pathways beyond complement activation are also involved in the spectrum of preeclampsia and HELLP syndrome. Second, eculizumab-containing serum was derived from a patient and therefore, we could not determine the amount of eculizumab needed to block complement-mediated cell killing. Last, our results need to be confirmed 318 in larger cohorts of pregnant women.

In conclusion, we have shown that preeclampsia with severe features along with classic and atypical HELLP syndrome may be considered, at least in part, a disease of excessive complement activation. The modified Ham test may be a promising tool to identify patients with increased complement activation who would benefit from complement inhibition by eculizumab. If confirmed in a larger cohort, the modified Ham test may be a valuable assay to select patients for such a clinical trial.

Example 6: Small Molecule Factor D Inhibitors Block Complement Activation in Paroxysmal Nocturnal Hemoglobinuria and Atypical Hemolytic Uremic Syndrome Introduction.

Factor D is a highly specific serine protease that cleaves factor B as its only substrate. It is the rate-limiting step of the alternative pathway of complement (APC). Therefore, factor D is a promising therapeutic target in diseases of excess activation of the APC, such as paroxysmal nocturnal hemoglobinuria (PNH) and atypical hemolytic uremic syndrome (aHUS). Terminal complement inhibition by eculizumab is currently the treatment of choice for PNH and aHUS. Eculizumab must be administered intravenously and indefinitely in PNH; moreover, up to 20% of PNH patients treated with eculizumab have symptomatic hemolysis due to extravascular hemolysis. GPI anchor protein deficient red cells from PNH patients or erythrocytes from animals can be used to test novel complement inhibitors for PNH; however, there are no in vitro assays available to model complement mediated attack in aHUS. Here, we demonstrate that the modified Ham test (PIGA null reagent cell line exposed to serum from aHUS patients) is the first reliable human, in vitro model for aHUS. In addition, we demonstrate that small molecule factor D inhibitors specifically block the APC in PNH and aHUS.

Method.

Three factor D inhibitors that reversibly bind factor D and are currently being developed were studied. We obtained blood samples from 5 PNH and 4 aHUS patients after written informed consent. Serum and erythrocytes from PNH patients on eculizumab were collected within 60 minutes of eculizumab administration. All three compounds were tested in half-log dilutions ranging from 0.001 µM to 10 µM. The binding affinity to factor D was determined by surface plasmon resonance (Biacore) analysis. The inhibitory effect on factor D protease was evaluated biochemically using a natural substrate consisting of C3b and the complement factor B. The inhibition of APC-mediated hemolysis was first evaluated with rabbit erythrocytes incubated with 8% normal human serum (NHS). The inhibition of APC-mediated C3 fragment deposition was also initially evaluated with rabbit erythrocytes incubated with 20% C5-depleted NHS (to mimic the effect of eculizumab) by flow cytometry. To confirm the observation with rabbit erythrocytes, erythrocytes from PNH patients were also tested in the hemolytic assay (20% acidified NHS). Regarding aHUS, the inhibitory effect of the compounds was evaluated in the recently described modified Ham test. Briefly, PIGA-null TF-1 cells were incubated with 20% of aHUS serum for 30 minutes at 37° C. and complement-mediated cell killing was evaluated using the cell proliferation reagent (WST-1). Absorbance was measured and expressed as a ratio to the heat-inactivated control (% non-viable cells).

Results.

Figure 17:
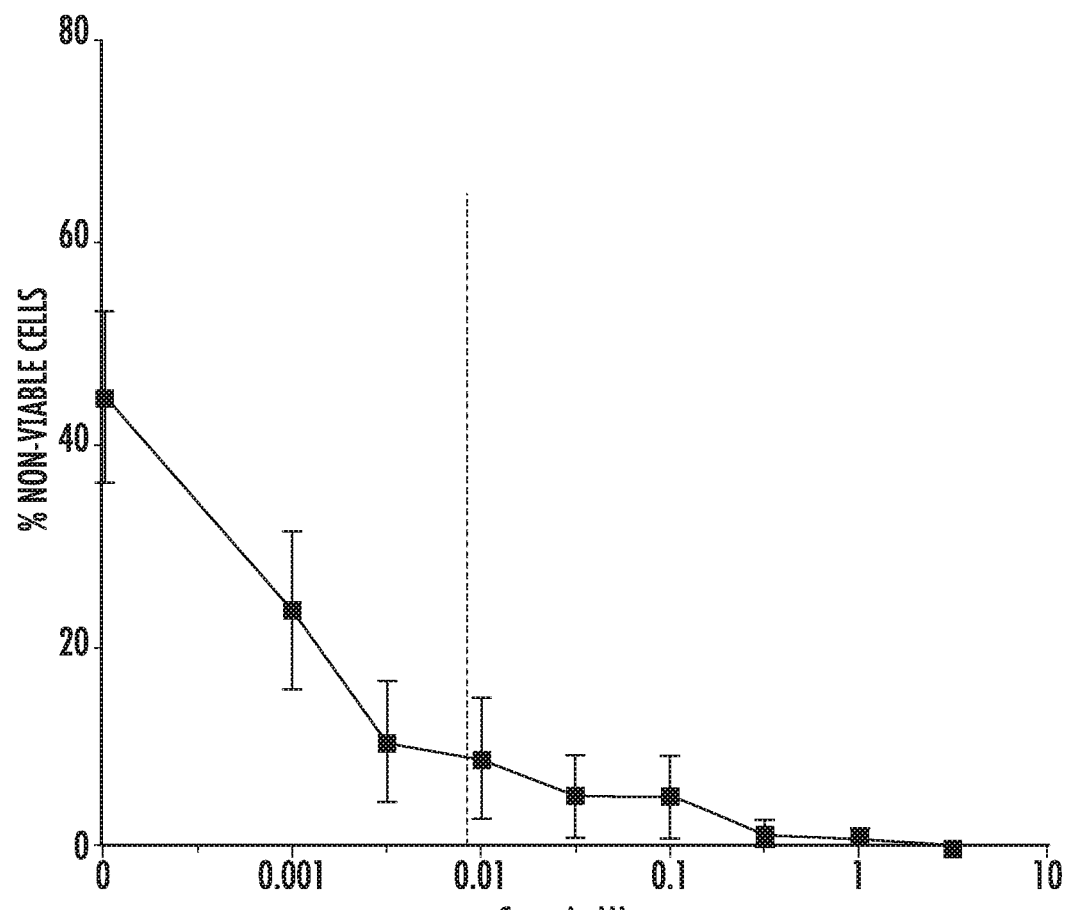
FIG. 17. The addition of a Factor D inhibitor caused significant dose-dependent reduction in the cell killing at concentration as low as 0.01 µM. Mean % non-viable cells before and after addition of the inhibitor are shown.

All 3 small molecules showed high binding affinity to human factor D and effectively inhibited factor D proteolytic activity in a dose dependent manner (mean $IC_{50}$ 9.8-20 nM). Similarly, we observed a dose-dependent inhibition of hemolysis on rabbit erythrocytes ($EC_{50}$ 9-17 nM). C3 fragment deposition on rabbit erythrocytes after incubation with C5-depleted serum was reduced to undetectable levels with all 3 compounds from concentrations of 0.1 µM and above. Next, we studied samples from 5 PNH patients (2 treatment naïve and 3 on eculizumab) and 4 aHUS patients (1 on eculizumab, 1 in acute phase and on eculizumab and 2 in remission). When tested effect on hemolysis with erythrocytes collected from PNH patients and acidified NHS, factor D inhibitors significantly reduced hemolysis in a dose-dependent manner from concentrations as low as 0.01 µM. Lastly, cell killing was observed as previously reported in the presence of the serum from aHUS patients in the modified Ham test and addition of factor D inhibitors caused significant dose-dependent reduction in the cell killing at concentration as low as 0.01 µM. Mean % non-viable cells before and after addition of an inhibitor is shown in FIG. 17.

Conclusions

We demonstrate that factor D inhibitors efficiently block hemolysis of PNH cells in vitro and mitigate the accumulation of C3 fragments. Importantly, our findings indicate that the recently described modified Ham test can be used as a preclinical model to test complement inhibitors in aHUS.

What is claimed is:

1. A method comprising the steps of:
    a. incubating serum obtained from a patient suspected of having antiphospholipid antibody syndrome (APS) with a plurality of GPI-AP deficient cells; and
    b. performing a cell viability assay on the cells from step (a).

2. A method for treating APS in a patient comprising the steps of administering an effective amount of an anticoagulant, statin, rituximab, and/or eculizumab to a patient diagnosed with APS according to a method comprising the steps of (a) incubating serum obtained from a patient suspected of having APS with a plurality of GPI-AP deficient cells; (b) performing a cell viability assay on the cells from step (a); and (c) diagnosing the patient as having APS based on a statistically significant increased difference of non-viable cells from the patient serum as compared to a control.

3. A method for treating APS in a patient comprising the step of administering an effective amount of an anticoagulant, statin, rituximab, and/or eculizumab to a patient diagnosed with APS based on the performance of a cell viability assay on a plurality of GPI-AP deficient that have been incubated with serum obtained from the patient, wherein the diagnosis is based on a statistically significant increased difference of non-viable cells from the patient serum as compared to a control.

4. A method for treating APS in a patient comprising the steps of:
    a. incubating serum obtained from a patient suspected of having APS with a plurality of GPI-AP deficient cells;
    b. performing a cell viability assay on the cells from step (a);
    c. diagnosing the patient as having APS based on a statistically significant increased difference of non-viable cells from the patient serum as compared to a control; and
    d. administering an effective amount of an anticoagulant, statin, rituximab, and/or eculizumab to the patient.

5. The method of claim 1, wherein the plurality of GPI-AP deficient cells is biochemically treated to remove GPI-AP.

6. The method of claim 1, wherein the plurality of GPI-AP deficient cells is a PIGA null mutant cell line.

7. The method of claim 1, wherein the cell viability assay is the WST-1 cell viability assay.

8. A method for treating APS in a patient comprising the step of administering an effective amount of a C5 inhibitor or a Factor D inhibitor to a patient diagnosed with APS based on the performance of a cell viability assay on a plurality of GPI-AP deficient that have been incubated with serum obtained from the patient, wherein the diagnosis is based on a statistically significant increased difference of non-viable cells from the patient serum as compared to a control.

9. The method of claim 8, wherein the C5 inhibitor comprises eculizumab and the Factor D inhibitor comprises ACH-4471.

10. A method for treating APS in a patient comprising the steps of:
    a. incubating serum obtained from a patient suspected of having APS with a plurality of GPI-AP deficient cells;
    b. performing a cell viability assay on the cells from step (a);
    c. diagnosing the patient as having APS based on a statistically significant increased difference of non-viable cells from the patient serum as compared to a control; and
    d. administering an effective amount of a C5 inhibitor or a Factor D inhibitor to the patient.

11. The method of claim 10, wherein the C5 inhibitor comprises eculizumab and the Factor D inhibitor comprises ACH-4471.

* * * * *